(12) United States Patent
Walter et al.

(10) Patent No.: US 7,767,625 B2
(45) Date of Patent: Aug. 3, 2010

(54) CARBOXANILIDES AS MICROBIOCIDES

(75) Inventors: Harald Walter, Basel (CH); Camilla Corsi, Basel (CH); Josef Ehrenfreund, Basel (CH); Clemens Lamberth, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 133 days.

(21) Appl. No.: 11/909,389

(22) PCT Filed: Mar. 21, 2006

(86) PCT No.: PCT/EP2006/002595

§ 371 (c)(1),
(2), (4) Date: Sep. 21, 2007

(87) PCT Pub. No.: WO2006/100039

PCT Pub. Date: Sep. 28, 2006

(65) Prior Publication Data

US 2008/0214532 A1    Sep. 4, 2008

(30) Foreign Application Priority Data

Mar. 23, 2005   (EP) .................................. 05006382

(51) Int. Cl.
*A01N 43/56* (2006.01)
*C07D 231/00* (2006.01)
(52) U.S. Cl. ................... 504/280; 548/374.1
(58) Field of Classification Search .............. 548/374.1; 514/422, 423; 504/280
See application file for complete search history.

(56) References Cited

U.S. PATENT DOCUMENTS

| 4,001,416 | A | 1/1977 | Pommer et al. |
| 4,134,987 | A | 1/1979 | Huppatz et al. |
| 4,742,074 | A | 5/1988 | Nishida et al. |
| 5,438,070 | A | 8/1995 | Eichen et al. |
| 6,365,620 | B2 * | 4/2002 | Eberle et al. ................ 514/422 |

FOREIGN PATENT DOCUMENTS

| EP | 0776889 | A | 6/1997 |
| WO | 93/11117 | A | 6/1993 |
| WO | 2004/018438 | A | 3/2004 |

* cited by examiner

*Primary Examiner*—Janet L Andres
*Assistant Examiner*—Binta M Robinson
(74) *Attorney, Agent, or Firm*—James Cueva

(57) ABSTRACT

Compounds of the formula (I) in which the substituents are as defined in claim 1 are suitable for use as microbiocides.

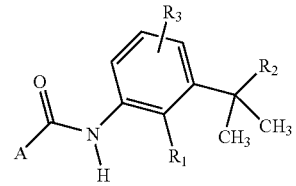

20 Claims, No Drawings

CARBOXANILIDES AS MICROBIOCIDES

This application is a 371 of International Application No. PCT/EP2006/002595 filed Mar. 21, 2006, which claims priority to EP 05006382.5 filed Mar. 23, 2005 the contents of which are incorporated herein by reference.

The present invention relates to novel microbiocidally active, in particular fungicidally active, carboxanilides. It further relates to intermediates used in the preparation of these compounds, to compositions which comprise these compounds and to their use in agriculture or horticulture for controlling or preventing infestation of plants by phytopathogenic microorganisms, preferably fungi.

Carboxanilides having microbiocidal activity are described, for example in WO 04/018438 and EP-0-589-301.

It has been found that novel carboxanilides with a specific ortho, meta-disubstitution pattern have microbiocidal activity.

The present invention thus provides compounds of the formula I

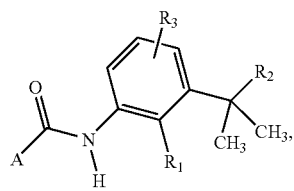

(I)

in which
$R_1$ is a $C_1$-$C_4$alkyl, $C_2$-$C_4$alkenyl or $C_2$-$C_4$alkynyl group; or
$R_1$ is a $C_1$-$C_4$alkyl, $C_2$-$C_4$alkenyl or $C_2$-$C_4$alkynyl group which is mono- or polysubstituted by halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$_4$)=N— and/or $R_5R_6$NN=C(H)—;
$R_4$, $R_5$ and $R_6$ independently of one another are hydrogen or $C_1$-$C_4$alkyl;
$R_2$ is a $C_1$-$C_6$alkyl group; or
$R_2$ is a $C_1$-$C_6$alkyl group which is mono- or polysubstituted by halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$_7$)=N— and/or $R_8R_9$NN=C(H)—;
$R_7$, $R_8$ and $R_9$ independently of one another are hydrogen or $C_1$-$C_4$alkyl;
$R_3$ is hydrogen or halogen;
A is $A_1$

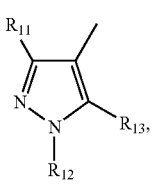

(A₁)

in which
$R_{11}$, $R_{12}$ and $R_{13}$ independently of one another are selected from hydrogen, halo, cyano, nitro, $C_1$-$C_4$alkyl, $C_1$-$C_4$haloalkyl, $C_1$-$C_4$alkoxy-$C_1$-$C_4$alkyl and $C_1$-$C_4$haloalkoxy-$C_1$-$C_4$alkyl, provided that at least one of $R_{11}$, $R_{12}$ and $R_{13}$ is not hydrogen;
or A is $A_2$

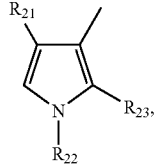

(A₂)

in which
$R_{21}$, $R_{22}$ and $R_{23}$ independently of one another are hydrogen, halo, cyano, nitro, $C_1$-$C_4$alkyl, $C_1$-$C_4$haloalkyl, $C_1$-$C_4$alkoxy-$C_1$-$C_4$alkyl or $C_1$-$C_4$haloalkoxy-$C_1$-$C_4$alkyl, with the proviso that at least one of $R_{11}$, $R_{12}$ and $R_{13}$ is not hydrogen;
or A is $A_3$

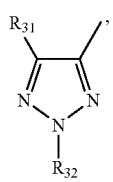

(A₃)

in which
$R_{31}$ and $R_{32}$ independently of one another are hydrogen, halo, cyano, nitro, $C_1$-$C_4$alkyl, $C_1$-$C_4$haloalkyl, $C_1$-$C_4$alkoxy-$C_1$-$C_4$alkyl or $C_1$-$C_4$haloalkoxy-$C_1$-$C_4$alkyl, with the proviso that at least one of $R_{31}$ and $R_{32}$ is not hydrogen;
or A is $A_4$

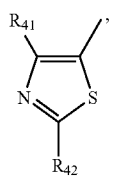

(A₄)

in which
$R_{41}$, and $R_{42}$ independently of one another are hydrogen, halo, cyano, nitro, $C_1$-$C_4$alkyl, $C_1$-$C_4$haloalkyl, $C_1$-$C_4$alkoxy-$C_1$-$C_4$alkyl or $C_1$-$C_4$haloalkoxy-$C_1$-$C_4$alkyl, with the proviso that at least one of $R_{41}$ and $R_{42}$ is not hydrogen;
or A is $A_5$

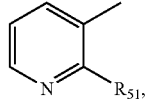

(A₅)

in which
$R_{51}$ is halo, cyano, nitro, $C_1$-$C_4$alkyl, $C_1$-$C_4$haloalkyl, $C_1$-$C_4$alkoxy-$C_1$-$C_4$alkyl or $C_1$-$C_4$haloalkoxy-$C_1$-$C_4$alkyl; or A is $A_6$

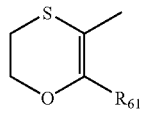

(A₆)

in which
$R_{61}$ is halo, cyano, nitro, $C_1$-$C_4$alkyl, $C_1$-$C_4$haloalkyl, $C_1$-$C_4$alkoxy-$C_1$-$C_4$alkyl or $C_1$-$C_4$haloalkoxy-$C_1$-$C_4$alkyl; and tautomers/isomers/enantiomers of these compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, isobutyl or tert-butyl. Alkoxy, alkenyl and alkynyl radicals are derived from the alkyl radicals mentioned. The alkenyl and alkynyl groups can be mono- or di-unsaturated.

Halogen is generally fluorine, chlorine, bromine or iodine, preferably fluorine, bromine or chlorine. This also applies, correspondingly, to halogen in combination with other meanings, such as haloalkyl or haloalkoxy.

Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloro-methyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In the context of the present invention "mono- or polysubstituted", for example in the definition of substituents $R_1$ and $R_2$, means typically monosubstituted to nine-times substituted, preferably monosubstituted to five-times substituted, more preferably mono-, double- or triple-substituted.

The compounds of the formula I may occur in different tautomeric forms, such as $I_I$ and $I_{II}$:

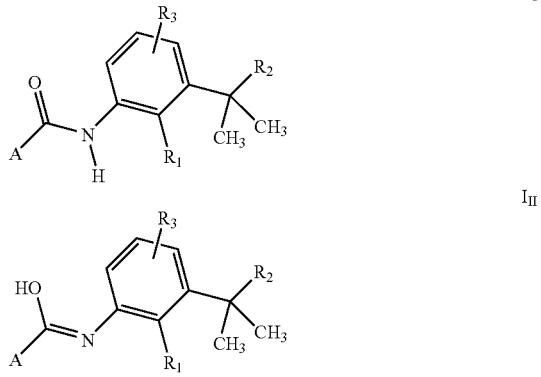

The invention covers all those tautomeric forms.

In a preferred group of compounds $R_1$ is a $C_1$-$C_4$alkyl, $C_2$-$C_4$alkenyl or $C_2$-$C_4$alkynyl group; or $R_1$ is a $C_1$-$C_4$alkyl, $C_2$-$C_4$alkenyl or $C_2$-$C_4$alkynyl group which is mono- or polysubstituted by halogen, hydroxy, methoxy, trifluoromethoxy, difluoromethoxy, cyano and/or nitro. More preferred compounds of the formula I are those in which $R_1$ is a $C_1$-$C_4$alkyl, $C_2$-$C_4$alkenyl or $C_2$-$C_4$alkynyl group. Most preferred compounds of the formula I are those in which $R_1$ is methyl, ethyl or vinyl.

Preference is furthermore given to those compounds of the formula I, in which $R_2$ is a $C_2$-$C_5$alkyl group; or $R_2$ is a $C_2$-$C_5$alkyl group which is mono- or polysubstituted by halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, $HC(OR_7)=N-$ and/or $R_8R_9NN=C(H)-$. More preferred compounds of the formula I are those in which $R_1$ is ethyl, iso-propyl, butyl, iso-butyl, pentyl, neopentyl Preference is furthermore given to those compounds of the formula I, in which $R_2$ is methyl.

Of particular interest are compounds of the formula I, in which $R_3$ is hydrogen or fluoro. In a preferred group of those compounds $R_3$ is hydrogen.

In preferred compounds of formula I $R_{11}$, $R_{12}$ and $R_{13}$ are, independently, selected from hydrogen, halogen, $C_1$-$C_4$alkyl, $C_1$-$C_4$haloalkyl and $C_1$-$C_4$alkoxy-$C_1$-$C_4$alkyl; provided that at least one of $R_{11}$, $R_{12}$ and $R_{13}$ is not hydrogen. More preferably $R_{11}$, $R_{12}$ and $R_{13}$ are, independently, selected from hydrogen, halogen, methyl, $C_1$-$C_2$haloalkyl and methoxymethyl; provided that at least one of $R_{11}$, $R_{12}$ and $R_{13}$ is not hydrogen.

In preferred compounds of formula I $R_{21}$, $R_{22}$ and $R_{23}$ are, independently, selected from hydrogen, halogen, $C_1$-$C_4$alkyl, $C_1$-$C_4$haloalkyl and $C_1$-$C_4$alkoxy-$C_1$-$C_4$alkyl; provided that at least one of $R_{21}$, $R_{22}$ and $R_{23}$ is not hydrogen. More preferably $R_{21}$, $R_{22}$ and $R_{23}$ are, independently, selected from hydrogen, halogen, methyl, $C_1$-$C_2$haloalkyl and methoxymethyl; provided that at least one of $R_{21}$, $R_{22}$ and $R_{23}$ is not hydrogen.

In preferred compounds of formula I $R_{31}$ and $R_{32}$ are, independently, selected from hydrogen, halogen, $C_1$-$C_4$alkyl, $C_1$-$C_4$haloalkyl and $C_1$-$C_4$alkoxy-$C_1$-$C_4$alkyl; provided that at least one of $R_{31}$ and $R_{32}$ is not hydrogen. More preferably $R_{31}$, $R_{32}$ and $R_{33}$ are, independently, selected from hydrogen, halogen, methyl, $C_1$-$C_2$haloalkyl and methoxymethyl; provided that at least one of $R_{31}$ and $R_{32}$ is not hydrogen.

In preferred compounds of formula I $R_{41}$ and $R_{42}$ are, independently, selected from hydrogen, halogen, $C_1$-$C_4$alkyl, $C_1$-$C_4$haloalkyl and $C_1$-$C_4$alkoxy-$C_1$-$C_4$alkyl; provided that at least one of $R_{41}$ and $R_{42}$ is not hydrogen. More preferably $R_{41}$ and $R_{42}$ are, independently, selected from hydrogen, halogen, methyl, $C_1$-$C_2$haloalkyl and methoxymethyl; provided that at least one of $R_{41}$ and $R_{42}$ is not hydrogen.

In preferred compounds of formula I $R_{51}$ and $R_{52}$ are, independently, selected from hydrogen, halogen, $C_1$-$C_4$alkyl, $C_1$-$C_4$haloalkyl and $C_1$-$C_4$alkoxy-$C_1$-$C_4$alkyl; provided that at least one of $R_{51}$ and $R_{52}$ is not hydrogen. More preferably $R_{51}$ and $R_{52}$ are, independently, selected from hydrogen, halogen, methyl, $C_1$-$C_2$haloalkyl and methoxymethyl; provided that at least one of $R_{51}$ and $R_{52}$ is not hydrogen.

Preferably A is $A_1$, $A_2$, $A_4$, $A_5$ or $A_6$. In another preferred group of compounds A is $A_1$, $A_2$, $A_3$, $A_4$ or $A_6$. In a more preferred group of compounds A is $A_1$, $A_2$, $A_4$ or $A_6$. Most preferably A is $A_1$, $A_2$ or $A_4$.

In a particular preferred group of compounds A is $A_1$, wherein $R_{13}$ is hydrogen.

In another particular preferred group of compounds A is $A_1$, wherein $R_{11}$ is $C_1$-$C_4$alkyl or $C_1$-$C_4$haloalkyl; $R_{12}$ is $C_1$-$C_4$alkyl; and $R_{13}$ is hydrogen or halogen.

In another particular preferred group of compounds A is $A_2$, wherein $R_{21}$ is $C_1$-$C_4$alkyl or $C_1$-$C_4$haloalkyl; $R_{22}$ is $C_1$-$C_4$alkyl; and $R_{23}$ is hydrogen or halogen.

In yet another particular preferred group of compounds A is $A_3$, wherein $R_{31}$ is $C_1$-$C_4$alkyl or $C_1$-$C_4$haloalkyl; and $R_{32}$ is $C_1$-$C_4$alkyl.

In yet another particular preferred group of compounds A is $A_4$, wherein $R_{41}$ is $C_1$-$C_4$alkyl or $C_1$-$C_4$haloalkyl; and $R_{42}$ is $C_1$-$C_4$alkyl.

In yet another particular preferred group of compounds A is $A_5$, wherein $R_{51}$ is halogen or $C_1$-$C_4$haloalkyl.

In yet another particular preferred group of compounds A is $A_6$, wherein $R_{61}$ is $C_1$-$C_4$alkyl or $C_1$-$C_4$haloalkyl.

Compounds of formula I may be prepared by reacting a compound of formula Ia

in which A is as defined under formula I, and R* is halogen, hydroxy or $C_{1-6}$ alkoxy, preferably chloro; with a compound of formula II

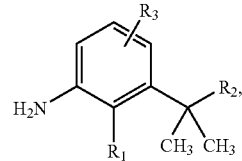

in which $R_1$, $R_2$ and $R_3$ are as defined under formula I; in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride, N,N'-dicyclohexylcarbodiimide or 1,1'-carbonyldiimidazole, may be used.

The intermediates of the formula II

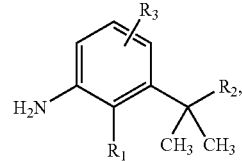

in which $R_1$, $R_2$ and $R_3$ are as defined under formula I; are novel and were developed specifically for the preparation of the compounds of the formula I. Accordingly, they also form part of the subject-matter of the present invention.

In preferred intermediates of formula II, $R_1$ is a $C_1$-$C_4$alkyl, $C_2$-$C_4$alkenyl or $C_2$-$C_4$alkynyl group; or $R_1$ is a $C_1$-$C_4$alkyl, $C_2$-$C_4$alkenyl or $C_2$-$C_4$alkynyl group which is mono- or polysubstituted by halogen, hydroxy, methoxy, trifluoromethoxy, difluoromethoxy, cyano and nitro. More preferred intermediates of the formula II are those in which $R_1$ is a $C_1$-$C_4$alkyl, $C_2$-$C_4$alkenyl or $C_2$-$C_4$alkynyl group. Most preferred intermediates of the formula II are those in which $R_1$ is methyl, ethyl or vinyl. Preference is furthermore given to those intermediates of the formula II, in which $R_2$ is methyl, ethyl, iso-propyl, butyl, iso-butyl, pentyl, neopentyl. Of particular interest are intermediates of the formula II, in which $R_3$ is hydrogen or fluoro. In a preferred group of those intermediates of the formula II $R_3$ is hydrogen.

Intermediates of the formula II, in which $R_1$, $R_2$ and $R_3$ are as defined under formula I; may be prepared according to the following reaction schemes (scheme 1A, 1B and 1C).

Intermediates of the formula IIa (intermediates of formula II, in which $R_1$ is methyl) may be prepared by reaction scheme 1A.

Scheme 1A:

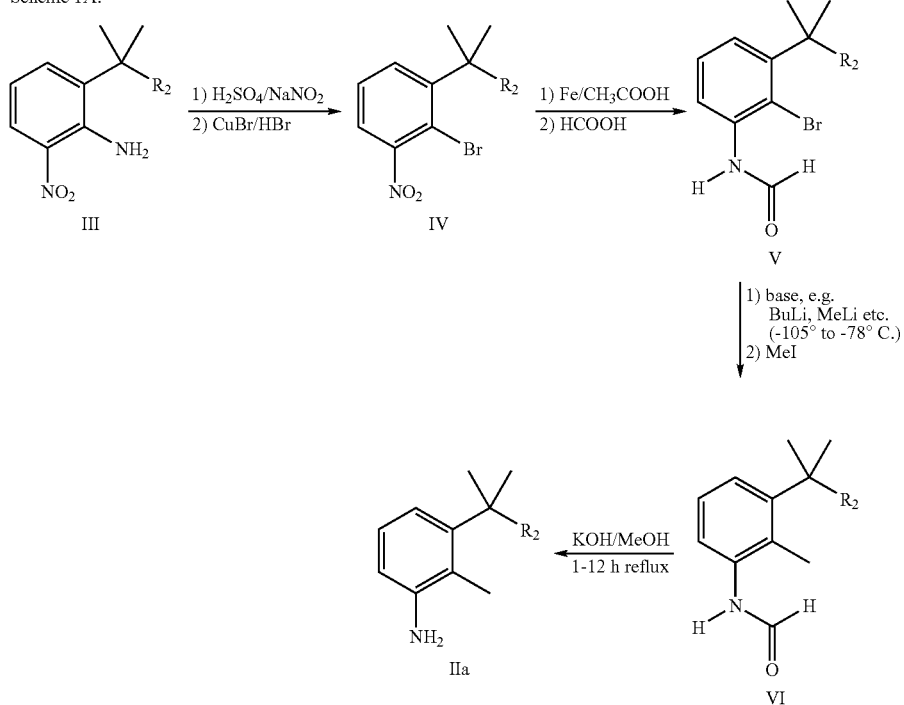

In the first step a compound of formula III is reacted with sulfuric acid and sodium nitrite to form a diazonium salt. Treatment of the diazonium salt with Cu(I)bromide gives the arylbromide of formula IV. Reduction of the compound of formula IV with Fe under Béchamp conditions and formylation of the resulting amino group using formic acid gives a formanilide of formula V. The reaction of the compound of formula V with a strong base, such as butyl lithium, forms a dianion, which is subsequently methylated to the compound of formula VI. Basic hydrolysis of the compound of formula VI with potassiumhydroxide gives the anilines of formula IIa.

Intermediates of the formula IIb (intermediates of formula II, in which $R_1$ is ethyl or propyl) or formula IIc (intermediates of formula II, in which $R_1$ is vinyl or allyl) may be prepared according to reaction scheme 1B.

Scheme 1B:

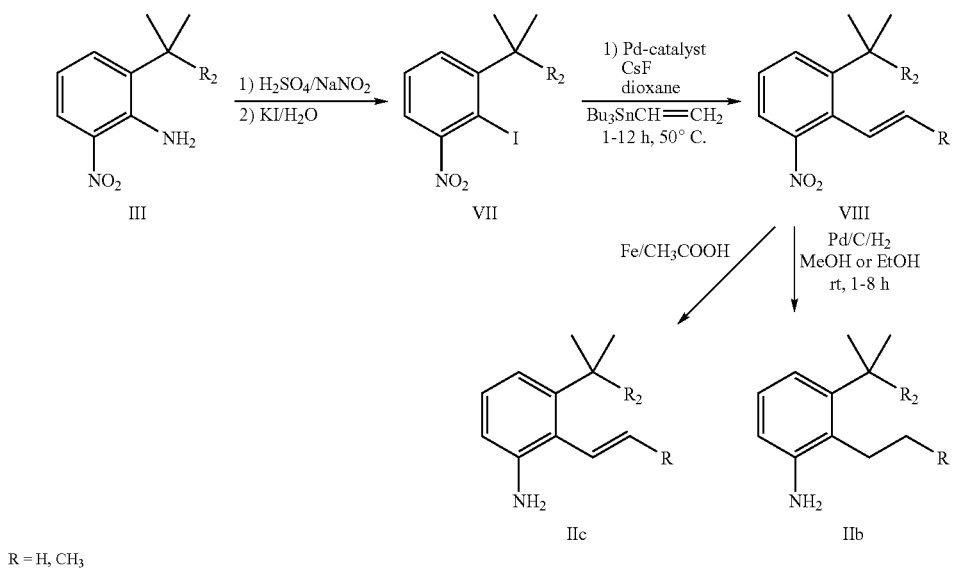

In the first step a compound of formula III is reacted with sulfuric acid and sodium nitrite to form a diazonium salt. Treatment of the diazonium salt with potassium iodide gives the aryliodide of formula VII (common "Sandmeyer"-reaction). In the next step the aryliodide of formula VII undergo a "Stille"-coupling reaction using standard "Fu" conditions (e.g tributylvinyistannane, a Pd-catalyst and cesiumfluoride) resulting in the vinylsubstituted aromatic compound of formula VIII. The compound of formula VIII can either be transformed into a partially reduced compound of formula IIc (using metallic iron as the reducing agent) or can be transformed after complete reduction (using a Pd metal catalyst) into a bisalkylated compound of formula IIb.

Intermediates of the formula IIb (intermediates of formula II, in which $R_1$ is ethyl or propyl) or formula IId (intermediates of formula II, in which $R_1$ is vinyl or allyl) may be prepared according to reaction scheme 1C.

For preparing all further compounds of the formula I functionalized according to the definitions of $R_1$, $R_2$, $R_3$ and A, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are

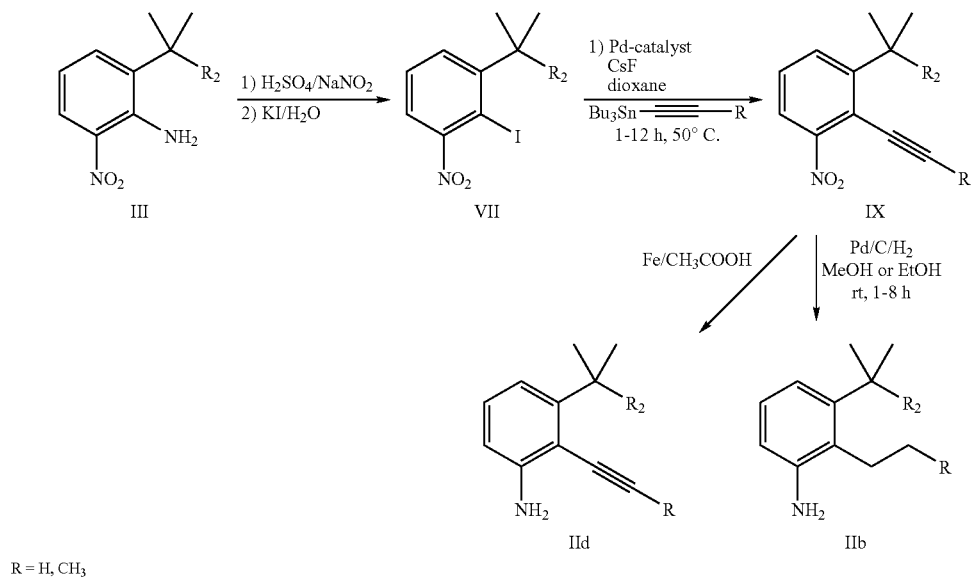

Scheme 1C:

R = H, CH₃

The above described iodide of formula VII is treated with an trisbutylacetinylstannane in the presence of an Pd-catalyst and cesiumfluoride (modified "Stille"-coupling) to give a compound of formula IX, which bears an acetylenic moiety at the aromatic ring. The compound of formula VIII can either be transformed into a partially reduced compound of formula IId (using metallic iron as the reducing agent) or can be transformed after complete reduction (using a Pd metal catalyst, such as palladium on charcoal) into a bisalkylated compound of formula IIb.

The synthesis of the compounds of the general formulae III, IV and VII can be accomplished by the use of already published analogous procedures: Rec. Trav. Chim. 1952, 71, 321; J. Chem. Soc. Perkin. Trans 2, 1973, 6, 848; and Acta Chem. Scandinavica 1976, 30B, 141.

The compounds of the formula Ia are known and partially commercially available. They can be prepared analogously as described, for example, in WO 00/09482, WO 02/38542, WO 04/018438, EP-0-589-301, WO 93/11117 and Arch. of Pharm. Res. 2000, 23(4), 315-323.

advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-pro-duct racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective iso-mer, for example enantiomer or diastereomer, or isomer mixture, for example enantiomer mixture or diastereomer mixture, if the individual components have a different biological activity.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus* luminescens, *Xenorhabdus* nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA(c), CryIF, CryIF(a2), CryIIA(b), CryIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Boligard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® and Protecta®.

Further examples of such transgenic crops are:

1. Bt11 Maize from Syngenta Seeds SAS, Chemin de I'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de I'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de I'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO03/018810.
4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example Phakopsora pachyrhizi, which is also referred to as Asian soybean rust, and those of the family Pucciniaceae, particularly those of the genus *Puccinia* such as *Puccinia* graminis, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus*, *A. flavus*, *A. terrus*, *A. nidulans* and *A. niger*, those causing Blastomycosis such as *Blastomyces dermatitidis*; those causing Candidiasis such as *Candida albicans*, *C. glabrata*, *C. tropicalis*, *C. parapsilosis*, *C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera*, *Rhizomucor pusillus* and *Rhizopus arrhizus*. Further examples are *Fusarium* Spp such as *Fusarium oxysporum* and *Fusarium* solani and *Scedosporium* Spp such as *Scedosporium apiospermum* and *Scedosporium prolificans*. Still further examples are Microsporum Spp, *Trichophyton* Spp, *Epidermophyton* Spp, *Mucor* Spp, Sporothorix Spp, Phialophora Spp, *Cladosporium* Spp, *Petriellidium* spp, Paracoccidioides Spp and *Histoplasma* Spp.

The following non-limiting Examples illustrate the above-described invention in greater detail without limiting it.

PREPARATION EXAMPLES

Example P1

Preparation of 3-(1,1-dimethypropyl)-2-methyl-phenylamine 4.13 g (17.1 mmol) 2-bromo-3-(1,1-dimethylpropyl)phenylamine and 7 ml of 98% formic acid are heated at 80° C. for 3.5 hours. After cooling 300 ml water are added. The water phase is extracted with ethylacetate and after drying of the organic phase over sodiumsulfate, the organic solvent is evaporated in a water jet vacuum. The obtained product is purified by crystallisation in hexane. This gives 4.17 g N-(2-Bromo-3-(1,1-dimethylpropyl)phenyl)formamide as a brownish solid (m.p. 88-89° C., 90% of theory).

3.4 g (12.6 mmol) N-(2-bromo-3-(1,1-dimethyl)propylphenyl)form-amide is dissolved in a mixture of 120 ml of a 1:1 mixture of diethylether and tetrahydrofurane. After cooling to −78° C. 9.47 ml (15.16 mmol) of a 1,6-molar methyllithium solution in Et$_2$O are added dropwise. After stirring at −78° C. for 2 hours the solution is cooled to −100° C. and 10.26 ml (16.42 mmol) of a 1.6 molar n-butyllithium solution in Et$_2$O are added dropwise. After stirring at −100° C. for 3 hours, the mixture is warmed up to −78° C. and 3.05 g (21.47 mmol) methyliodide dissolved in 14 ml of absolute tetrahydrofurane are added dropwise. After stirring for 1 h at −78° C. the mixture is slowly warmed up to room temperature. Cold water is added to the reaction mixture and the water phase is extracted with ethylacetate. After drying over sodium sulfate and evaporation of the solvent in a water jet vacuum, the reaction product is purified by column chromatography over silicagel (eluant: hexane/ethyl-acetate 2:1). 1,91 g N-(2-Methyl-3-(1,1-dimethylpropyl)phenyl)formamide are obtained in the form of colourless crystals (m.p. 51-53° C., 74% of theory).

2,21 g (10.77 mmol) N-(2-methyl-3-(1,1-dimethylpropyl) phenyl)form-amide, 1,42 g (21.54 mmol) 85% potassium hydroxide and 9 ml methanol are heated under stirring at reflux temperature for 15 hours. After cooling 100 ml of water is added and the reaction mixture is extracted with ethylacetate. After drying of the organic phase over sodium sulfate and evaporation of the solvent in a water jet vacuum, the product is purified by destillation (bp. ca. 70° C., 13,33 Pa). This gives 1.7 g of 2-Methyl-3-(1,1-dimethylpropyl)phenylamine in the form of a colourless oil (89% of theory).

Example P2

Preparation of 3-(1,1-dimethylpropyl)-2-vinyl-phenylamine 2,63 g (8,24 mmol) 1-(1,1-dimethylpropyl)-2-iodo-3-nitrobenzene and 3,4 g (10,72 mmol) tributylvinyltin are dissolved in 30 ml of absolute dioxane. After this, 0,11 g (0,12 mmol) tris(dibenzylideneacetone)dipalladium ($Pd_2(dba)_3$), 0,12 g (0,24 mmol) bis(tri-t-butylphoshine) palladium (Pd[P(tet.butyl)$_3$]$_2$) and 2,75 g (18,14 mmol) CsF are added. The reaction mixture is heated to 50° C. for 2 hours under nitrogen atmosphere. After cooling ice water is added and the resulting mixture is extracted with ethylacetate. After drying of the organic phase over sodium sulfate and evaporation of the solvent in a water jet vacuum the reaction product is purified by column chromatography over silicagel (eluent: hexane/methylene-chloride 5:1). This gives 1,75 g 1-(1,1-dimethyl)-2-vinyl-3-nitrobenzene in the form of a yellow oil (97% of theory).

A mixture of 1,75 g (8,05 mmol) 1-(1,1-dimethyl)-2-vinyl-3-nitrobenzene, 0.67 g iron powder, 7 ml water, 7,6 ml n-propanol and 2,4 ml of acetic acid is heated at 85° C. for 6 hours. After this 200 ml water are added. The reaction mixture is extracted with ethylacetate. The organic phase is washed with brine and dried over sodium sulfate. After evaporation of the solvent in a water jet vacuum the reaction product is purified by column chromatography over silicagel (eluent: cyclohexane/methylenechloride 2:1). This gives 0,55 g 3-(1,1-dimethylpropyl)-2-vinyl-phenylamine in the form of a slightly brownish oil (36% of theory).

Example P3

Preparation of 3-tert-butyl-2-ethyl-phenylamine

In a hydrogenation apparatus, a mixture of 1,5 g (8,55 mmol) 1-tert-butyl-2-vinyl-3-nitrobenzene and 250 mg 5% Pd/C and 20 ml of absolute methanol is hydrogenated at room temperature for 2,5 hours. The catalyst is filtered off and the solvent is evaporated in a water jet vacuum. The crude reaction product can be used directly for further chemical transformations. This gives 1,5 g 3-tert-butyl-2-vinyl-phenylamine in the form of a slightly brownish liquid (98% of theory).

Example P4

Preparation of 3-tert-butyl-2-prop-1-ynyl-phenylamine 3,55 g (11,65 mmol) 1-tert-butyl-2-iodo-3-nitrobenzene and 4,6 g (13.97 mmol) (tributylprop-1-ynyl)tin is dissolved in 20 ml of absolute dioxane. After this 0,16 g (0,175 mmol) tris(dibenzylideneacetone)dipalladium ($Pd_2(dba)_3$), 0,18 g(0,35 mmol) bis(tri-t-butylphosphine) palladium (Pd[P(tet.butyl)$_3$]$_2$) and 3,9 g (25,6 mmol) cesiumfluoride (CsF) are added. The resulting mixture is heated under stirring at 50-55° C. for 6 hours under nitrogen atmosphere. The reaction mixture is cooled, ice water is added and the mixture is extracted with ethylacetate. After drying of the organic solvent over sodium sulfate and evaporation of the solvent in a water jet vacuum, the reaction product is purified by column chromatography over silicagel (eluent: hexane). This gives 2.4 g 1-tert-butyl-2-prop-1-ynyl-3-nitrobenzene in the form of a yellow liquid (94% of theory).

A mixture of 1,5 g (6,9 mmol) 1-tert-butyl-2-propin-1-ynyl-3-nitrobenzene, 0,6 g iron powder, 6 ml water, 6,6 ml n-propanol and 2 ml acetic acid is heated at 85° C. for 3 hours. After this 100 ml water are added. The reaction mixture is extracted ethylacetate. The organic phase is washed with brine and dried over sodium sulfate. After evaporation of the solvent the reaction product is purified by column chromatography over silicagel (eluent: hexane/ethylacetate 10:1). This gives 0,7 g 3-tert-butyl-2-prop-1-ynyl-phenylamine in the form of a slightly brownish oil (54% of theory).

Example P5

Preparation of 1-Methyl-3-trifluoromethyl-1H-pyrazole-4-carboxylic acid (3-tert-butyl-2-vinylphenyl) amide 197 mg (1,01 mmol) 1-methyl-3-trifluoromethyl-1H-pyrazole-4-carboxylic acid and 135 mg (1,07 mmol) oxalylic acid chloride are dissolved in 8 ml methylenechloride. The solution is stirred for 3 hours at room temperature in the presence of a catalytic amount of dimethylformamide (DMF). After this the solution is slowly added to a solution consisting of 180 mg (1,01 mmol) 3-tert-butyl-2-vinyl-phenylamine, 155 mg (1,52 mmol) triethylamine and 7 ml methylenechloride. The resulting reaction mixture is then stirred at room temperature for 16 hours. After removal of the solvent in a water jet vacuum, the residue is purified by flash chromatography over silicagel (eluent: hexane/ethylacetate 2:1). This gives 0,27 g 1-methyl-3-trifluoromethyl-1H-pyrazole-4-carboxylic acid (3-tert-butyl-2-vinylphenyl)amide in the form of a colourless solid (m.p. 118-119° C.; 76% of theory).

Preferred compounds of the formula I are listed in the tables below.

TABLE 1

Compounds of formula IA

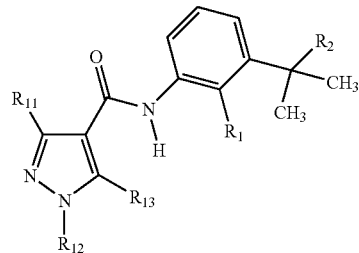

(IA)

| Compound Number | $R_1$ | $R_2$ | $R_{11}$ | $R_{12}$ | $R_{13}$ |
|---|---|---|---|---|---|
| 1.1 | $CH_3$ | $CH_3$ | $CF_3$ | $CH_3$ | H |
| 1.2 | $CH_3$ | $CH_2CH_3$ | $CF_3$ | $CH_3$ | H |
| 1.3 | $CH_3$ | $CH(CH_3)_2$ | $CF_3$ | $CH_3$ | H |
| 1.4 | $CH_3$ | $CH_2CH(CH_3)_2$ | $CF_3$ | $CH_3$ | H |
| 1.5 | $CH_3$ | $CH_2C(CH_3)_3$ | $CF_3$ | $CH_3$ | H |
| 1.6 | $CH_3$ | $CH_3$ | $CF_2H$ | $CH_3$ | H |
| 1.7 | $CH_3$ | $CH_2CH_3$ | $CF_2H$ | $CH_3$ | H |
| 1.8 | $CH_3$ | $CH(CH_3)_2$ | $CF_2H$ | $CH_3$ | H |
| 1.9 | $CH_3$ | $CH_2CH(CH_3)_2$ | $CF_2H$ | $CH_3$ | H |
| 1.10 | $CH_3$ | $CH_2C(CH_3)_3$ | $CF_2H$ | $CH_3$ | H |
| 1.11 | $CH_3$ | $CH_3$ | $CFH_2$ | $CH_3$ | H |

TABLE 1-continued

Compounds of formula IA

| Compound Number | R₁ | R₂ | R₁₁ | R₁₂ | R₁₃ |
|---|---|---|---|---|---|
| 1.12 | CH₃ | CH₂CH₃ | CFH₂ | CH₃ | H |
| 1.13 | CH₃ | CH(CH₃)₂ | CFH₂ | CH₃ | H |
| 1.14 | CH₃ | CH₂CH(CH₃)₂ | CFH₂ | CH₃ | H |
| 1.15 | CH₃ | CH₂C(CH₃)₃ | CFH₂ | CH₃ | H |
| 1.16 | CH₃ | CH₃ | CH₃ | CH₃ | H |
| 1.17 | CH₃ | CH₂CH₃ | CH₃ | CH₃ | H |
| 1.18 | CH₃ | CH(CH₃)₂ | CH₃ | CH₃ | H |
| 1.19 | CH₃ | CH₂CH(CH₃)₂ | CH₃ | CH₃ | H |
| 1.20 | CH₃ | CH₂C(CH₃)₃ | CH₃ | CH₃ | H |
| 1.21 | CH₃ | CH₃ | CH₃ | CH₃ | F |
| 1.22 | CH₃ | CH₂CH₃ | CH₃ | CH₃ | F |
| 1.23 | CH₃ | CH(CH₃)₂ | CH₃ | CH₃ | F |
| 1.24 | CH₃ | CH₂CH(CH₃)₂ | CH₃ | CH₃ | F |
| 1.25 | CH₃ | CH₂C(CH₃)₃ | CH₃ | CH₃ | F |
| 1.26 | CH₂CH₃ | CH₃ | CF₃ | CH₃ | H |
| 1.27 | CH₂CH₃ | CH₂CH₃ | CF₃ | CH₃ | H |
| 1.28 | CH₂CH₃ | CH(CH₃)₂ | CF₃ | CH₃ | H |
| 1.29 | CH₂CH₃ | CH₂CH(CH₃)₂ | CF₃ | CH₃ | H |
| 1.30 | CH₂CH₃ | CH₂C(CH₃)₃ | CF₃ | CH₃ | H |
| 1.31 | CH₂CH₃ | CH₃ | CF₂H | CH₃ | H |
| 1.32 | CH₂CH₃ | CH₂CH₃ | CF₂H | CH₃ | H |
| 1.33 | CH₂CH₃ | CH(CH₃)₂ | CF₂H | CH₃ | H |
| 1.34 | CH₂CH₃ | CH₂CH(CH₃)₂ | CF₂H | CH₃ | H |
| 1.35 | CH₂CH₃ | CH₂C(CH₃)₃ | CF₂H | CH₃ | H |
| 1.36 | CH₂CH₃ | CH₃ | CFH₂ | CH₃ | H |
| 1.37 | CH₂CH₃ | CH₂CH₃ | CFH₂ | CH₃ | H |
| 1.38 | CH₂CH₃ | CH(CH₃)₂ | CFH₂ | CH₃ | H |
| 1.39 | CH₂CH₃ | CH₂CH(CH₃)₂ | CFH₂ | CH₃ | H |
| 1.40 | CH₂CH₃ | CH₂C(CH₃)₃ | CFH₂ | CH₃ | H |
| 1.41 | CH₂CH₃ | CH₃ | CH₃ | CH₃ | H |
| 1.42 | CH₂CH₃ | CH₂CH₃ | CH₃ | CH₃ | H |
| 1.43 | CH₂CH₃ | CH(CH₃)₂ | CH₃ | CH₃ | H |
| 1.44 | CH₂CH₃ | CH₂CH(CH₃)₂ | CH₃ | CH₃ | H |
| 1.45 | CH₂CH₃ | CH₂C(CH₃)₃ | CH₃ | CH₃ | H |
| 1.46 | CH₂CH₃ | CH₃ | CH₃ | CH₃ | F |
| 1.47 | CH₂CH₃ | CH₂CH₃ | CH₃ | CH₃ | F |
| 1.48 | CH₂CH₃ | CH(CH₃)₂ | CH₃ | CH₃ | F |
| 1.49 | CH₂CH₃ | CH₂CH(CH₃)₂ | CH₃ | CH₃ | F |
| 1.50 | CH₂CH₃ | CH₂C(CH₃)₃ | CH₃ | CH₃ | F |
| 1.51 | CH₂CH₂CH₃ | CH₃ | CF₃ | CH₃ | H |
| 1.52 | CH₂CH₂CH₃ | CH₂CH₃ | CF₃ | CH₃ | H |
| 1.53 | CH₂CH₂CH₃ | CH₃ | CF₂H | CH₃ | H |
| 1.54 | CH₂CH₂CH₃ | CH₂CH₃ | CF₂H | CH₃ | H |
| 1.55 | CH₂CH₂CH₃ | CH₃ | CFH₂ | CH₃ | H |
| 1.56 | CH₂CH₂CH₃ | CH₂CH₃ | CFH₂ | CH₃ | H |
| 1.57 | CH₂CH₂CH₃ | CH₃ | CH₃ | CH₃ | H |
| 1.58 | CH₂CH₂CH₃ | CH₂CH₃ | CH₃ | CH₃ | H |
| 1.59 | CH₂CH₂CH₃ | CH₃ | CH₃ | CH₃ | F |
| 1.60 | CH₂CH₂CH₃ | CH₂CH₃ | CH₃ | CH₃ | F |
| 1.61 | CH=CH₂ | CH₃ | CF₃ | CH₃ | H |
| 1.62 | CH=CH₂ | CH₂CH₃ | CF₃ | CH₃ | H |
| 1.63 | CH=CH₂ | CH(CH₃)₂ | CF₃ | CH₃ | H |
| 1.64 | CH=CH₂ | CH₂CH(CH₃)₂ | CF₃ | CH₃ | H |
| 1.65 | CH=CH₂ | CH₂C(CH₃)₃ | CF₃ | CH₃ | H |
| 1.66 | CH=CH₂ | CH₃ | CF₂H | CH₃ | H |
| 1.67 | CH=CH₂ | CH₂CH₃ | CF₂H | CH₃ | H |
| 1.68 | CH=CH₂ | CH(CH₃)₂ | CF₂H | CH₃ | H |
| 1.69 | CH=CH₂ | CH₂CH(CH₃)₂ | CF₂H | CH₃ | H |
| 1.70 | CH=CH₂ | CH₂C(CH₃)₃ | CF₂H | CH₃ | H |
| 1.71 | CH=CH₂ | CH₃ | CFH₂ | CH₃ | H |
| 1.72 | CH=CH₂ | CH₂CH₃ | CFH₂ | CH₃ | H |
| 1.73 | CH=CH₂ | CH(CH₃)₂ | CFH₂ | CH₃ | H |
| 1.74 | CH=CH₂ | CH₂CH(CH₃)₂ | CFH₂ | CH₃ | H |
| 1.75 | CH=CH₂ | CH₂C(CH₃)₃ | CFH₂ | CH₃ | H |
| 1.76 | CH=CH₂ | CH₃ | CH₃ | CH₃ | H |
| 1.77 | CH=CH₂ | CH₂CH₃ | CH₃ | CH₃ | H |
| 1.78 | CH=CH₂ | CH(CH₃)₂ | CH₃ | CH₃ | H |
| 1.79 | CH=CH₂ | CH₂CH(CH₃)₂ | CH₃ | CH₃ | H |
| 1.80 | CH=CH₂ | CH₂C(CH₃)₃ | CH₃ | CH₃ | H |
| 1.81 | CH=CH₂ | CH₃ | CH₃ | CH₃ | F |
| 1.82 | CH=CH₂ | CH₂CH₃ | CH₃ | CH₃ | F |
| 1.83 | CH=CH₂ | CH(CH₃)₂ | CH₃ | CH₃ | F |
| 1.84 | CH=CH₂ | CH₂CH(CH₃)₂ | CH₃ | CH₃ | F |
| 1.85 | CH=CH₂ | CH₂C(CH₃)₃ | CH₃ | CH₃ | F |
| 1.86 | C≡CH | CH₃ | CF₃ | CH₃ | H |
| 1.87 | C≡CH | CH₂CH₃ | CF₃ | CH₃ | H |
| 1.88 | C≡CH | CH(CH₃)₂ | CF₃ | CH₃ | H |
| 1.89 | C≡CH | CH₂CH(CH₃)₂ | CF₃ | CH₃ | H |
| 1.90 | C≡CH | CH₂C(CH₃)₃ | CF₃ | CH₃ | H |
| 1.91 | C≡CH | CH₃ | CF₂H | CH₃ | H |
| 1.92 | C≡CH | CH₂CH₃ | CF₂H | CH₃ | H |
| 1.93 | C≡CH | CH(CH₃)₂ | CF₂H | CH₃ | H |
| 1.94 | C≡CH | CH₂CH(CH₃)₂ | CF₂H | CH₃ | H |
| 1.95 | C≡CH | CH₂C(CH₃)₃ | CF₂H | CH₃ | H |
| 1.96 | C≡CH | CH₃ | CFH₂ | CH₃ | H |
| 1.97 | C≡CH | CH₂CH₃ | CFH₂ | CH₃ | H |
| 1.98 | C≡CH | CH(CH₃)₂ | CFH₂ | CH₃ | H |
| 1.99 | C≡CH | CH₂CH(CH₃)₂ | CFH₂ | CH₃ | H |
| 1.100 | C≡CH | CH₂C(CH₃)₃ | CFH₂ | CH₃ | H |
| 1.101 | C≡CH | CH₃ | CH₃ | CH₃ | H |
| 1.102 | C≡CH | CH₂CH₃ | CH₃ | CH₃ | H |
| 1.103 | C≡CH | CH(CH₃)₂ | CH₃ | CH₃ | H |
| 1.104 | C≡CH | CH₂CH(CH₃)₂ | CH₃ | CH₃ | H |
| 1.105 | C≡CH | CH₂C(CH₃)₃ | CH₃ | CH₃ | H |
| 1.106 | C≡CH | CH₃ | CH₃ | CH₃ | F |
| 1.107 | C≡CH | CH₂CH₃ | CH₃ | CH₃ | F |
| 1.108 | C≡CH | CH(CH₃)₂ | CH₃ | CH₃ | F |
| 1.109 | C≡CH | CH₂CH(CH₃)₂ | CH₃ | CH₃ | F |
| 1.110 | C≡CH | CH₂C(CH₃)₃ | CH₃ | CH₃ | F |
| 1.111 | C≡CCH₃ | CH₃ | CF₃ | CH₃ | H |
| 1.112 | C≡CCH₃ | CH₂CH₃ | CF₃ | CH₃ | H |
| 1.113 | C≡CCH₃ | CH(CH₃)₂ | CF₃ | CH₃ | H |
| 1.114 | C≡CCH₃ | CH₂CH(CH₃)₂ | CF₃ | CH₃ | H |
| 1.115 | C≡CCH₃ | CH₂C(CH₃)₃ | CF₃ | CH₃ | H |
| 1.116 | C≡CCH₃ | CH₃ | CF₂H | CH₃ | H |
| 1.117 | C≡CCH₃ | CH₂CH₃ | CF₂H | CH₃ | H |
| 1.118 | C≡CCH₃ | CH(CH₃)₂ | CF₂H | CH₃ | H |
| 1.119 | C≡CCH₃ | CH₂CH(CH₃)₂ | CF₂H | CH₃ | H |
| 1.120 | C≡CCH₃ | CH₂C(CH₃)₃ | CF₂H | CH₃ | H |
| 1.121 | C≡CCH₃ | CH₃ | CFH₂ | CH₃ | H |
| 1.122 | C≡CCH₃ | CH₂CH₃ | CFH₂ | CH₃ | H |
| 1.123 | C≡CCH₃ | CH(CH₃)₂ | CFH₂ | CH₃ | H |
| 1.124 | C≡CCH₃ | CH₂CH(CH₃)₂ | CFH₂ | CH₃ | H |
| 1.125 | C≡CCH₃ | CH₂C(CH₃)₃ | CFH₂ | CH₃ | H |
| 1.126 | C≡CCH₃ | CH₃ | CH₃ | CH₃ | H |
| 1.127 | C≡CCH₃ | CH₂CH₃ | CH₃ | CH₃ | H |
| 1.128 | C≡CCH₃ | CH(CH₃)₂ | CH₃ | CH₃ | H |
| 1.129 | C≡CCH₃ | CH₂CH(CH₃)₂ | CH₃ | CH₃ | H |
| 1.130 | C≡CCH₃ | CH₂C(CH₃)₃ | CH₃ | CH₃ | H |
| 1.131 | C≡CCH₃ | CH₃ | CH₃ | CH₃ | F |

TABLE 1-continued

Compounds of formula IA (IA)

Structure: Pyrazole carboxamide with $R_{11}$ at 3-position, $R_{13}$ at 5-position, $R_{12}$ on N1, connected via C(=O)NH to phenyl ring bearing $R_1$ (ortho) and C(CH$_3$)(CH$_3$)$R_2$ (meta).

| Compound Number | $R_1$ | $R_2$ | $R_{11}$ | $R_{12}$ | $R_{13}$ |
|---|---|---|---|---|---|
| 1.132 | C≡CCH$_3$ | CH$_2$CH$_3$ | CH$_3$ | CH$_3$ | F |
| 1.133 | C≡CCH$_3$ | CH(CH$_3$)$_2$ | CH$_3$ | CH$_3$ | F |
| 1.134 | C≡CCH$_3$ | CH$_2$CH(CH$_3$)$_2$ | CH$_3$ | CH$_3$ | F |
| 1.135 | C≡CCH$_3$ | CH$_2$C(CH$_3$)$_3$ | CH$_3$ | CH$_3$ | F |

TABLE 2

Compound of formula IB (IB)

Structure: Pyrrole carboxamide with $R_{21}$ at 4-position, $R_{23}$ at 2-position, $R_{22}$ on N1, connected via C(=O)NH to phenyl ring bearing $R_1$ (ortho) and C(CH$_3$)(CH$_3$)$R_2$ (meta).

| Compound Number | $R_1$ | $R_2$ | $R_{21}$ | $R_{22}$ | $R_{23}$ |
|---|---|---|---|---|---|
| 2.1 | CH$_3$ | CH$_3$ | CF$_3$ | CH$_3$ | H |
| 2.2 | CH$_3$ | CH$_2$CH$_3$ | CF$_3$ | CH$_3$ | H |
| 2.3 | CH$_3$ | CH(CH$_3$)$_2$ | CF$_3$ | CH$_3$ | H |
| 2.4 | CH$_3$ | CH$_2$CH(CH$_3$)$_2$ | CF$_3$ | CH$_3$ | H |
| 2.5 | CH$_3$ | CH$_2$C(CH$_3$)$_3$ | CF$_3$ | CH$_3$ | H |
| 2.6 | CH$_3$ | CH$_3$ | CF$_2$H | CH$_3$ | H |
| 2.7 | CH$_3$ | CH$_2$CH$_3$ | CF$_2$H | CH$_3$ | H |
| 2.8 | CH$_3$ | CH(CH$_3$)$_2$ | CF$_2$H | CH$_3$ | H |
| 2.9 | CH$_3$ | CH$_2$CH(CH$_3$)$_2$ | CF$_2$H | CH$_3$ | H |
| 2.10 | CH$_3$ | CH$_2$C(CH$_3$)$_3$ | CF$_2$H | CH$_3$ | H |
| 2.11 | CH$_3$ | CH$_3$ | CFH$_2$ | CH$_3$ | H |
| 2.12 | CH$_3$ | CH$_2$CH$_3$ | CFH$_2$ | CH$_3$ | H |
| 2.13 | CH$_3$ | CH(CH$_3$)$_2$ | CFH$_2$ | CH$_3$ | H |
| 2.14 | CH$_3$ | CH$_2$CH(CH$_3$)$_2$ | CFH$_2$ | CH$_3$ | H |
| 2.15 | CH$_3$ | CH$_2$C(CH$_3$)$_3$ | CFH$_2$ | CH$_3$ | H |
| 2.16 | CH$_3$ | CH$_3$ | CH$_3$ | CH$_3$ | H |
| 2.17 | CH$_3$ | CH$_2$CH$_3$ | CH$_3$ | CH$_3$ | H |
| 2.18 | CH$_3$ | CH(CH$_3$)$_2$ | CH$_3$ | CH$_3$ | H |
| 2.19 | CH$_3$ | CH$_2$CH(CH$_3$)$_2$ | CH$_3$ | CH$_3$ | H |
| 2.20 | CH$_3$ | CH$_2$C(CH$_3$)$_3$ | CH$_3$ | CH$_3$ | H |
| 2.21 | CH$_3$ | CH$_3$ | CH$_3$ | CH$_3$ | F |
| 2.22 | CH$_3$ | CH$_2$CH$_3$ | CH$_3$ | CH$_3$ | F |
| 2.23 | CH$_3$ | CH(CH$_3$)$_2$ | CH$_3$ | CH$_3$ | F |
| 2.24 | CH$_3$ | CH$_2$CH(CH$_3$)$_2$ | CH$_3$ | CH$_3$ | F |
| 2.25 | CH$_3$ | CH$_2$C(CH$_3$)$_3$ | CH$_3$ | CH$_3$ | F |
| 2.26 | CH$_2$CH$_3$ | CH$_3$ | CF$_3$ | CH$_3$ | H |
| 2.27 | CH$_2$CH$_3$ | CH$_2$CH$_3$ | CF$_3$ | CH$_3$ | H |
| 2.28 | CH$_2$CH$_3$ | CH(CH$_3$)$_2$ | CF$_3$ | CH$_3$ | H |
| 2.29 | CH$_2$CH$_3$ | CH$_2$CH(CH$_3$)$_2$ | CF$_3$ | CH$_3$ | H |
| 2.30 | CH$_2$CH$_3$ | CH$_2$C(CH$_3$)$_3$ | CF$_3$ | CH$_3$ | H |
| 2.31 | CH$_2$CH$_3$ | CH$_3$ | CF$_2$H | CH$_3$ | H |
| 2.32 | CH$_2$CH$_3$ | CH$_2$CH$_3$ | CF$_2$H | CH$_3$ | H |
| 2.33 | CH$_2$CH$_3$ | CH(CH$_3$)$_2$ | CF$_2$H | CH$_3$ | H |
| 2.34 | CH$_2$CH$_3$ | CH$_2$CH(CH$_3$)$_2$ | CF$_2$H | CH$_3$ | H |
| 2.35 | CH$_2$CH$_3$ | CH$_2$C(CH$_3$)$_3$ | CF$_2$H | CH$_3$ | H |
| 2.36 | CH$_2$CH$_3$ | CH$_3$ | CFH$_2$ | CH$_3$ | H |
| 2.37 | CH$_2$CH$_3$ | CH$_2$CH$_3$ | CFH$_2$ | CH$_3$ | H |
| 2.38 | CH$_2$CH$_3$ | CH(CH$_3$)$_2$ | CFH$_2$ | CH$_3$ | H |
| 2.39 | CH$_2$CH$_3$ | CH$_2$CH(CH$_3$)$_2$ | CFH$_2$ | CH$_3$ | H |
| 2.40 | CH$_2$CH$_3$ | CH$_2$C(CH$_3$)$_3$ | CFH$_2$ | CH$_3$ | H |
| 2.41 | CH$_2$CH$_3$ | CH$_3$ | CH$_3$ | CH$_3$ | H |
| 2.42 | CH$_2$CH$_3$ | CH$_2$CH$_3$ | CH$_3$ | CH$_3$ | H |
| 2.43 | CH$_2$CH$_3$ | CH(CH$_3$)$_2$ | CH$_3$ | CH$_3$ | H |
| 2.44 | CH$_2$CH$_3$ | CH$_2$CH(CH$_3$)$_2$ | CH$_3$ | CH$_3$ | H |
| 2.45 | CH$_2$CH$_3$ | CH$_2$C(CH$_3$)$_3$ | CH$_3$ | CH$_3$ | H |
| 2.46 | CH$_2$CH$_3$ | CH$_3$ | CH$_3$ | CH$_3$ | F |
| 2.47 | CH$_2$CH$_3$ | CH$_2$CH$_3$ | CH$_3$ | CH$_3$ | F |
| 2.48 | CH$_2$CH$_3$ | CH(CH$_3$)$_2$ | CH$_3$ | CH$_3$ | F |
| 2.49 | CH$_2$CH$_3$ | CH$_2$CH(CH$_3$)$_2$ | CH$_3$ | CH$_3$ | F |
| 2.50 | CH$_2$CH$_3$ | CH$_2$C(CH$_3$)$_3$ | CH$_3$ | CH$_3$ | F |
| 2.51 | CH$_2$CH$_2$CH$_3$ | CH$_3$ | CF$_3$ | CH$_3$ | H |
| 2.52 | CH$_2$CH$_2$CH$_3$ | CH$_2$CH$_3$ | CF$_3$ | CH$_3$ | H |
| 2.53 | CH$_2$CH$_2$CH$_3$ | CH$_3$ | CF$_2$H | CH$_3$ | H |
| 2.54 | CH$_2$CH$_2$CH$_3$ | CH$_2$CH$_3$ | CF$_2$H | CH$_3$ | H |
| 2.55 | CH$_2$CH$_2$CH$_3$ | CH$_3$ | CFH$_2$ | CH$_3$ | H |
| 2.56 | CH$_2$CH$_2$CH$_3$ | CH$_2$CH$_3$ | CFH$_2$ | CH$_3$ | H |
| 2.57 | CH$_2$CH$_2$CH$_3$ | CH$_3$ | CH$_3$ | CH$_3$ | H |
| 2.58 | CH$_2$CH$_2$CH$_3$ | CH$_2$CH$_3$ | CH$_3$ | CH$_3$ | H |
| 2.59 | CH$_2$CH$_2$CH$_3$ | CH$_3$ | CH$_3$ | CH$_3$ | F |
| 2.60 | CH$_2$CH$_2$CH$_3$ | CH$_2$CH$_3$ | CH$_3$ | CH$_3$ | F |
| 2.61 | CH=CH$_2$ | CH$_3$ | CF$_3$ | CH$_3$ | H |
| 2.62 | CH=CH$_2$ | CH$_2$CH$_3$ | CF$_3$ | CH$_3$ | H |
| 2.63 | CH=CH$_2$ | CH(CH$_3$)$_2$ | CF$_3$ | CH$_3$ | H |
| 2.64 | CH=CH$_2$ | CH$_2$CH(CH$_3$)$_2$ | CF$_3$ | CH$_3$ | H |
| 2.65 | CH=CH$_2$ | CH$_2$C(CH$_3$)$_3$ | CF$_3$ | CH$_3$ | H |
| 2.66 | CH=CH$_2$ | CH$_3$ | CF$_2$H | CH$_3$ | H |
| 2.67 | CH=CH$_2$ | CH$_2$CH$_3$ | CF$_2$H | CH$_3$ | H |
| 2.68 | CH=CH$_2$ | CH(CH$_3$)$_2$ | CF$_2$H | CH$_3$ | H |
| 2.69 | CH=CH$_2$ | CH$_2$CH(CH$_3$)$_2$ | CF$_2$H | CH$_3$ | H |
| 2.70 | CH=CH$_2$ | CH$_2$C(CH$_3$)$_3$ | CF$_2$H | CH$_3$ | H |
| 2.71 | CH=CH$_2$ | CH$_3$ | CFH$_2$ | CH$_3$ | H |
| 2.72 | CH=CH$_2$ | CH$_2$CH$_3$ | CFH$_2$ | CH$_3$ | H |
| 2.73 | CH=CH$_2$ | CH(CH$_3$)$_2$ | CFH$_2$ | CH$_3$ | H |
| 2.74 | CH=CH$_2$ | CH$_2$CH(CH$_3$)$_2$ | CFH$_2$ | CH$_3$ | H |
| 2.75 | CH=CH$_2$ | CH$_2$C(CH$_3$)$_3$ | CFH$_2$ | CH$_3$ | H |
| 2.76 | CH=CH$_2$ | CH$_3$ | CH$_3$ | CH$_3$ | H |
| 2.77 | CH=CH$_2$ | CH$_2$CH$_3$ | CH$_3$ | CH$_3$ | H |
| 2.78 | CH=CH$_2$ | CH(CH$_3$)$_2$ | CH$_3$ | CH$_3$ | H |
| 2.79 | CH=CH$_2$ | CH$_2$CH(CH$_3$)$_2$ | CH$_3$ | CH$_3$ | H |
| 2.80 | CH=CH$_2$ | CH$_2$C(CH$_3$)$_3$ | CH$_3$ | CH$_3$ | H |
| 2.81 | CH=CH$_2$ | CH$_3$ | CH$_3$ | CH$_3$ | F |
| 2.82 | CH=CH$_2$ | CH$_2$CH$_3$ | CH$_3$ | CH$_3$ | F |
| 2.83 | CH=CH$_2$ | CH(CH$_3$)$_2$ | CH$_3$ | CH$_3$ | F |
| 2.84 | CH=CH$_2$ | CH$_2$CH(CH$_3$)$_2$ | CH$_3$ | CH$_3$ | F |
| 2.85 | CH=CH$_2$ | CH$_2$C(CH$_3$)$_3$ | CH$_3$ | CH$_3$ | F |
| 2.86 | C≡CH | CH$_3$ | CF$_3$ | CH$_3$ | H |
| 2.87 | C≡CH | CH$_2$CH$_3$ | CF$_3$ | CH$_3$ | H |
| 2.88 | C≡CH | CH(CH$_3$)$_2$ | CF$_3$ | CH$_3$ | H |
| 2.89 | C≡CH | CH$_2$CH(CH$_3$)$_2$ | CF$_3$ | CH$_3$ | H |
| 2.90 | C≡CH | CH$_2$C(CH$_3$)$_3$ | CF$_3$ | CH$_3$ | H |
| 2.91 | C≡CH | CH$_3$ | CF$_2$H | CH$_3$ | H |

TABLE 2-continued

Compound of formula IB

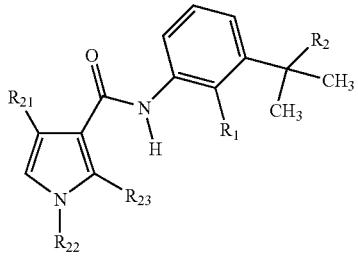

(IB)

| Compound Number | $R_1$ | $R_2$ | $R_{21}$ | $R_{22}$ | $R_{23}$ |
|---|---|---|---|---|---|
| 2.92 | C≡CH | $CH_2CH_3$ | $CF_2H$ | $CH_3$ | H |
| 2.93 | C≡CH | $CH(CH_3)_2$ | $CF_2H$ | $CH_3$ | H |
| 2.94 | C≡CH | $CH_2CH(CH_3)_2$ | $CF_2H$ | $CH_3$ | H |
| 2.95 | C≡CH | $CH_2C(CH_3)_3$ | $CF_2H$ | $CH_3$ | H |
| 2.96 | C≡CH | $CH_3$ | $CFH_2$ | $CH_3$ | H |
| 2.97 | C≡CH | $CH_2CH_3$ | $CFH_2$ | $CH_3$ | H |
| 2.98 | C≡CH | $CH(CH_3)_2$ | $CFH_2$ | $CH_3$ | H |
| 2.99 | C≡CH | $CH_2CH(CH_3)_2$ | $CFH_2$ | $CH_3$ | H |
| 2.100 | C≡CH | $CH_2C(CH_3)_3$ | $CFH_2$ | $CH_3$ | H |
| 2.101 | C≡CH | $CH_3$ | $CH_3$ | $CH_3$ | H |
| 2.102 | C≡CH | $CH_2CH_3$ | $CH_3$ | $CH_3$ | H |
| 2.103 | C≡CH | $CH(CH_3)_2$ | $CH_3$ | $CH_3$ | H |
| 2.104 | C≡CH | $CH_2CH(CH_3)_2$ | $CH_3$ | $CH_3$ | H |
| 2.105 | C≡CH | $CH_2C(CH_3)_3$ | $CH_3$ | $CH_3$ | H |
| 2.106 | C≡CH | $CH_3$ | $CH_3$ | $CH_3$ | F |
| 2.107 | C≡CH | $CH_2CH_3$ | $CH_3$ | $CH_3$ | F |
| 2.108 | C≡CH | $CH(CH_3)_2$ | $CH_3$ | $CH_3$ | F |
| 2.109 | C≡CH | $CH_2CH(CH_3)_2$ | $CH_3$ | $CH_3$ | F |
| 2.110 | C≡CH | $CH_2C(CH_3)_3$ | $CH_3$ | $CH_3$ | F |
| 2.111 | C≡CCH_3 | $CH_3$ | $CF_3$ | $CH_3$ | H |
| 2.112 | C≡CCH_3 | $CH_2CH_3$ | $CF_3$ | $CH_3$ | H |
| 2.113 | C≡CCH_3 | $CH(CH_3)_2$ | $CF_3$ | $CH_3$ | H |
| 2.114 | C≡CCH_3 | $CH_2CH(CH_3)_2$ | $CF_3$ | $CH_3$ | H |
| 2.115 | C≡CCH_3 | $CH_2C(CH_3)_3$ | $CF_3$ | $CH_3$ | H |
| 2.116 | C≡CCH_3 | $CH_3$ | $CF_2H$ | $CH_3$ | H |
| 2.117 | C≡CCH_3 | $CH_2CH_3$ | $CF_2H$ | $CH_3$ | H |
| 2.118 | C≡CCH_3 | $CH(CH_3)_2$ | $CF_2H$ | $CH_3$ | H |
| 2.119 | C≡CCH_3 | $CH_2CH(CH_3)_2$ | $CF_2H$ | $CH_3$ | H |
| 2.120 | C≡CCH_3 | $CH_2C(CH_3)_3$ | $CF_2H$ | $CH_3$ | H |
| 2.121 | C≡CCH_3 | $CH_3$ | $CFH_2$ | $CH_3$ | H |
| 2.122 | C≡CCH_3 | $CH_2CH_3$ | $CFH_2$ | $CH_3$ | H |
| 2.123 | C≡CCH_3 | $CH(CH_3)_2$ | $CFH_2$ | $CH_3$ | H |
| 2.124 | C≡CCH_3 | $CH_2CH(CH_3)_2$ | $CFH_2$ | $CH_3$ | H |
| 2.125 | C≡CCH_3 | $CH_2C(CH_3)_3$ | $CFH_2$ | $CH_3$ | H |
| 2.126 | C≡CCH_3 | $CH_3$ | $CH_3$ | $CH_3$ | H |
| 2.127 | C≡CCH_3 | $CH_2CH_3$ | $CH_3$ | $CH_3$ | H |
| 2.128 | C≡CCH_3 | $CH(CH_3)_2$ | $CH_3$ | $CH_3$ | H |
| 2.129 | C≡CCH_3 | $CH_2CH(CH_3)_2$ | $CH_3$ | $CH_3$ | H |
| 2.130 | C≡CCH_3 | $CH_2C(CH_3)_3$ | $CH_3$ | $CH_3$ | H |
| 2.131 | C≡CCH_3 | $CH_3$ | $CH_3$ | $CH_3$ | F |
| 2.132 | C≡CCH_3 | $CH_2CH_3$ | $CH_3$ | $CH_3$ | F |
| 2.133 | C≡CCH_3 | $CH(CH_3)_2$ | $CH_3$ | $CH_3$ | F |
| 2.134 | C≡CCH_3 | $CH_2CH(CH_3)_2$ | $CH_3$ | $CH_3$ | F |
| 2.135 | C≡CCH_3 | $CH_2C(CH_3)_3$ | $CH_3$ | $CH_3$ | F |

TABLE 3

Compounds of Formula IC

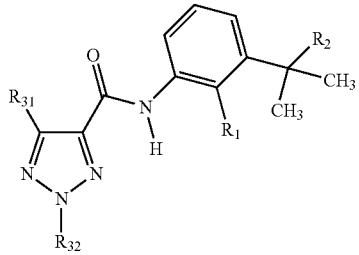

(IC)

| Compound Number | $R_1$ | $R_2$ | $R_{31}$ | $R_{32}$ |
|---|---|---|---|---|
| 3.1 | $CH_3$ | $CH_3$ | $CF_3$ | $CH_3$ |
| 3.2 | $CH_3$ | $CH_2CH_3$ | $CF_3$ | $CH_3$ |
| 3.3 | $CH_3$ | $CH(CH_3)_2$ | $CF_3$ | $CH_3$ |
| 3.4 | $CH_3$ | $CH_2CH(CH_3)_2$ | $CF_3$ | $CH_3$ |
| 3.5 | $CH_3$ | $CH_2C(CH_3)_3$ | $CF_3$ | $CH_3$ |
| 3.6 | $CH_3$ | $CH_3$ | $CF_2H$ | $CH_3$ |
| 3.7 | $CH_3$ | $CH_2CH_3$ | $CF_2H$ | $CH_3$ |
| 3.8 | $CH_3$ | $CH(CH_3)_2$ | $CF_2H$ | $CH_3$ |
| 3.9 | $CH_3$ | $CH_2CH(CH_3)_2$ | $CF_2H$ | $CH_3$ |
| 3.10 | $CH_3$ | $CH_2C(CH_3)_3$ | $CF_2H$ | $CH_3$ |
| 3.11 | $CH_3$ | $CH_3$ | $CFH_2$ | $CH_3$ |
| 3.12 | $CH_3$ | $CH_2CH_3$ | $CFH_2$ | $CH_3$ |
| 3.13 | $CH_3$ | $CH(CH_3)_2$ | $CFH_2$ | $CH_3$ |
| 3.14 | $CH_3$ | $CH_2CH(CH_3)_2$ | $CFH_2$ | $CH_3$ |
| 3.15 | $CH_3$ | $CH_2C(CH_3)_3$ | $CFH_2$ | $CH_3$ |
| 3.16 | $CH_3$ | $CH_3$ | $CH_3$ | $CH_3$ |
| 3.17 | $CH_3$ | $CH_2CH_3$ | $CH_3$ | $CH_3$ |
| 3.18 | $CH_3$ | $CH(CH_3)_2$ | $CH_3$ | $CH_3$ |
| 3.19 | $CH_3$ | $CH_2CH(CH_3)_2$ | $CH_3$ | $CH_3$ |
| 3.20 | $CH_3$ | $CH_2C(CH_3)_3$ | $CH_3$ | $CH_3$ |
| 3.21 | $CH_2CH_3$ | $CH_3$ | $CF_3$ | $CH_3$ |
| 3.22 | $CH_2CH_3$ | $CH_2CH_3$ | $CF_3$ | $CH_3$ |
| 3.23 | $CH_2CH_3$ | $CH(CH_3)_2$ | $CF_3$ | $CH_3$ |
| 3.24 | $CH_2CH_3$ | $CH_2CH(CH_3)_2$ | $CF_3$ | $CH_3$ |
| 3.25 | $CH_2CH_3$ | $CH_2C(CH_3)_3$ | $CF_3$ | $CH_3$ |
| 3.26 | $CH_2CH_3$ | $CH_3$ | $CF_2H$ | $CH_3$ |
| 3.27 | $CH_2CH_3$ | $CH_2CH_3$ | $CF_2H$ | $CH_3$ |
| 3.28 | $CH_2CH_3$ | $CH(CH_3)_2$ | $CF_2H$ | $CH_3$ |
| 3.29 | $CH_2CH_3$ | $CH_2CH(CH_3)_2$ | $CF_2H$ | $CH_3$ |
| 3.30 | $CH_2CH_3$ | $CH_2C(CH_3)_3$ | $CF_2H$ | $CH_3$ |
| 3.31 | $CH_2CH_3$ | $CH_3$ | $CFH_2$ | $CH_3$ |
| 3.32 | $CH_2CH_3$ | $CH_2CH_3$ | $CFH_2$ | $CH_3$ |
| 3.33 | $CH_2CH_3$ | $CH(CH_3)_2$ | $CFH_2$ | $CH_3$ |
| 3.34 | $CH_2CH_3$ | $CH_2CH(CH_3)_2$ | $CFH_2$ | $CH_3$ |
| 3.35 | $CH_2CH_3$ | $CH_2C(CH_3)_3$ | $CFH_2$ | $CH_3$ |
| 3.36 | $CH_2CH_3$ | $CH_3$ | $CH_3$ | $CH_3$ |
| 3.37 | $CH_2CH_3$ | $CH_2CH_3$ | $CH_3$ | $CH_3$ |
| 3.38 | $CH_2CH_3$ | $CH(CH_3)_2$ | $CH_3$ | $CH_3$ |
| 3.39 | $CH_2CH_3$ | $CH_2CH(CH_3)_2$ | $CH_3$ | $CH_3$ |
| 3.40 | $CH_2CH_3$ | $CH_2C(CH_3)_3$ | $CH_3$ | $CH_3$ |
| 3.41 | $CH_2CH_2CH_3$ | $CH_3$ | $CF_3$ | $CH_3$ |
| 3.42 | $CH_2CH_2CH_3$ | $CH_2CH_3$ | $CF_3$ | $CH_3$ |
| 3.43 | $CH_2CH_2CH_3$ | $CH_3$ | $CF_2H$ | $CH_3$ |
| 3.44 | $CH_2CH_2CH_3$ | $CH_2CH_3$ | $CF_2H$ | $CH_3$ |
| 3.45 | $CH_2CH_2CH_3$ | $CH_3$ | $CF_2H$ | $CH_3$ |
| 3.46 | $CH_2CH_2CH_3$ | $CH_2CH_3$ | $CFH_2$ | $CH_3$ |
| 3.47 | $CH_2CH_2CH_3$ | $CH_3$ | $CH_3$ | $CH_3$ |
| 3.48 | $CH_2CH_2CH_3$ | $CH_2CH_3$ | $CH_3$ | $CH_3$ |
| 3.49 | CH=CH_2 | $CH_3$ | $CF_3$ | $CH_3$ |
| 3.50 | CH=CH_2 | $CH_2CH_3$ | $CF_3$ | $CH_3$ |
| 3.51 | CH=CH_2 | $CH(CH_3)_2$ | $CF_3$ | $CH_3$ |
| 3.52 | CH=CH_2 | $CH_2CH(CH_3)_2$ | $CF_3$ | $CH_3$ |
| 3.53 | CH=CH_2 | $CH_2C(CH_3)_3$ | $CF_3$ | $CH_3$ |
| 3.54 | CH=CH_2 | $CH_3$ | $CF_2H$ | $CH_3$ |
| 3.55 | CH=CH_2 | $CH_2CH_3$ | $CF_2H$ | $CH_3$ |
| 3.56 | CH=CH_2 | $CH(CH_3)_2$ | $CF_2H$ | $CH_3$ |
| 3.57 | CH=CH_2 | $CH_2CH(CH_3)_2$ | $CF_2H$ | $CH_3$ |
| 3.58 | CH=CH_2 | $CH_2C(CH_3)_3$ | $CF_2H$ | $CH_3$ |
| 3.59 | CH=CH_2 | $CH_3$ | $CFH_2$ | $CH_3$ |
| 3.60 | CH=CH_2 | $CH_2CH_3$ | $CFH_2$ | $CH_3$ |

TABLE 3-continued

Compounds of Formula IC (IC)

| Compound Number | R$_1$ | R$_2$ | R$_{31}$ | R$_{32}$ |
|---|---|---|---|---|
| 3.61 | CH=CH$_2$ | CH(CH$_3$)$_2$ | CFH$_2$ | CH$_3$ |
| 3.62 | CH=CH$_2$ | CH$_2$CH(CH$_3$)$_2$ | CF$_2$H | CH$_3$ |
| 3.63 | CH=CH$_2$ | CH$_2$C(CH$_3$)$_3$ | CFH$_2$ | CH$_3$ |
| 3.64 | CH=CH$_2$ | CH$_3$ | CH$_3$ | CH$_3$ |
| 3.65 | CH=CH$_2$ | CH$_2$CH$_3$ | CH$_3$ | CH$_3$ |
| 3.66 | CH=CH$_2$ | CH(CH$_3$)$_2$ | CH$_3$ | CH$_3$ |
| 3.67 | CH=CH$_2$ | CH$_2$CH(CH$_3$)$_2$ | CH$_3$ | CH$_3$ |
| 3.68 | CH=CH$_2$ | CH$_2$C(CH$_3$)$_3$ | CH$_3$ | CH$_3$ |
| 3.69 | C≡CH | CH$_3$ | CF$_3$ | CH$_3$ |
| 3.70 | C≡CH | CH$_2$CH$_3$ | CF$_3$ | CH$_3$ |
| 3.71 | C≡CH | CH(CH$_3$)$_2$ | CF$_3$ | CH$_3$ |
| 3.72 | C≡CH | CH$_2$CH(CH$_3$)$_2$ | CF$_3$ | CH$_3$ |
| 3.73 | C≡CH | CH$_2$C(CH$_3$)$_3$ | CF$_3$ | CH$_3$ |
| 3.74 | C≡CH | CH$_3$ | CF$_2$H | CH$_3$ |
| 3.75 | C≡CH | CH$_2$CH$_3$ | CF$_2$H | CH$_3$ |
| 3.76 | C≡CH | CH(CH$_3$)$_2$ | CF$_2$H | CH$_3$ |
| 3.77 | C≡CH | CH$_2$CH(CH$_3$)$_2$ | CF$_2$H | CH$_3$ |
| 3.78 | C≡CH | CH$_2$C(CH$_3$)$_3$ | CF$_2$H | CH$_3$ |
| 3.79 | C≡CH | CH$_3$ | CFH$_2$ | CH$_3$ |
| 3.80 | C≡CH | CH$_2$CH$_3$ | CFH$_2$ | CH$_3$ |
| 3.81 | C≡CH | CH(CH$_3$)$_2$ | CFH$_2$ | CH$_3$ |
| 3.82 | C≡CH | CH$_2$CH(CH$_3$)$_2$ | CFH$_2$ | CH$_3$ |
| 3.83 | C≡CH | CH$_2$C(CH$_3$)$_3$ | CFH$_2$ | CH$_3$ |
| 3.84 | C≡CH | CH$_3$ | CH$_3$ | CH$_3$ |
| 3.85 | C≡CH | CH$_2$CH$_3$ | CH$_3$ | CH$_3$ |
| 3.86 | C≡CH | CH(CH$_3$)$_2$ | CH$_3$ | CH$_3$ |
| 3.87 | C≡CH | CH$_2$CH(CH$_3$)$_2$ | CH$_3$ | CH$_3$ |
| 3.88 | C≡CH | CH$_2$C(CH$_3$)$_3$ | CH$_3$ | CH$_3$ |
| 3.89 | C≡CCH$_3$ | CH$_3$ | CF$_3$ | CH$_3$ |
| 3.90 | C≡CCH$_3$ | CH$_2$CH$_3$ | CF$_3$ | CH$_3$ |
| 3.91 | C≡CCH$_3$ | CH(CH$_3$)$_2$ | CF$_3$ | CH$_3$ |
| 3.92 | C≡CCH$_3$ | CH$_2$CH(CH$_3$)$_2$ | CF$_3$ | CH$_3$ |
| 3.93 | C≡CCH$_3$ | CH$_2$C(CH$_3$)$_3$ | CF$_3$ | CH$_3$ |
| 3.94 | C≡CCH$_3$ | CH$_3$ | CF$_2$H | CH$_3$ |
| 3.95 | C≡CCH$_3$ | CH$_2$CH$_3$ | CF$_2$H | CH$_3$ |
| 3.96 | C≡CCH$_3$ | CH(CH$_3$)$_2$ | CF$_2$H | CH$_3$ |
| 3.97 | C≡CCH$_3$ | CH$_2$CH(CH$_3$)$_2$ | CF$_2$H | CH$_3$ |
| 3.98 | C≡CCH$_3$ | CH$_2$C(CH$_3$)$_3$ | CF$_2$H | CH$_3$ |
| 3.99 | C≡CCH$_3$ | CH$_3$ | CFH$_2$ | CH$_3$ |
| 3.100 | C≡CCH$_3$ | CH$_2$CH$_3$ | CFH$_2$ | CH$_3$ |
| 3.101 | C≡CCH$_3$ | CH(CH$_3$)$_2$ | CFH$_2$ | CH$_3$ |
| 3.102 | C≡CCH$_3$ | CH$_2$CH(CH$_3$)$_2$ | CFH$_2$ | CH$_3$ |
| 3.103 | C≡CCH$_3$ | CH$_2$C(CH$_3$)$_3$ | CFH$_2$ | CH$_3$ |
| 3.104 | C≡CCH$_3$ | CH$_3$ | CH$_3$ | CH$_3$ |
| 3.105 | C≡CCH$_3$ | CH$_2$CH$_3$ | CH$_3$ | CH$_3$ |
| 3.106 | C≡CCH$_3$ | CH(CH$_3$)$_2$ | CH$_3$ | CH$_3$ |
| 3.107 | C≡CCH$_3$ | CH$_2$CH(CH$_3$)$_2$ | CH$_3$ | CH$_3$ |
| 3.108 | C≡CCH$_3$ | CH$_2$C(CH$_3$)$_3$ | CH$_3$ | CH$_3$ |

TABLE 4

Compounds of formula ID (ID)

| Compound Number | R$_1$ | R$_2$ | R$_{41}$ | R$_{42}$ |
|---|---|---|---|---|
| 4.1 | CH$_3$ | CH$_3$ | CF$_3$ | CH$_3$ |
| 4.2 | CH$_3$ | CH$_2$CH$_3$ | CF$_3$ | CH$_3$ |
| 4.3 | CH$_3$ | CH(CH$_3$)$_2$ | CF$_3$ | CH$_3$ |
| 4.4 | CH$_3$ | CH$_2$CH(CH$_3$)$_2$ | CF$_3$ | CH$_3$ |
| 4.5 | CH$_3$ | CH$_2$C(CH$_3$)$_3$ | CF$_3$ | CH$_3$ |
| 4.6 | CH$_3$ | CH$_3$ | CH$_3$ | CH$_3$ |
| 4.7 | CH$_3$ | CH$_2$CH$_3$ | CH$_3$ | CH$_3$ |
| 4.8 | CH$_3$ | CH(CH$_3$)$_2$ | CH$_3$ | CH$_3$ |
| 4.9 | CH$_3$ | CH$_2$CH(CH$_3$)$_2$ | CH$_3$ | CH$_3$ |
| 4.10 | CH$_3$ | CH$_2$C(CH$_3$)$_3$ | CH$_3$ | CH$_3$ |
| 4.11 | CH$_3$ | CH$_3$ | CH$_2$CH$_3$ | CH$_3$ |
| 4.12 | CH$_3$ | CH$_2$CH$_3$ | CH$_2$CH$_3$ | CH$_3$ |
| 4.13 | CH$_3$ | CH(CH$_3$)$_2$ | CH$_2$CH$_3$ | CH$_3$ |
| 4.14 | CH$_3$ | CH$_2$CH(CH$_3$)$_2$ | CH$_2$CH$_3$ | CH$_3$ |
| 4.15 | CH$_3$ | CH$_2$C(CH$_3$)$_3$ | CH$_2$CH$_3$ | CH$_3$ |
| 4.16 | CH$_2$CH$_3$ | CH$_3$ | CF$_3$ | CH$_3$ |
| 4.17 | CH$_2$CH$_3$ | CH$_2$CH$_3$ | CF$_3$ | CH$_3$ |
| 4.18 | CH$_2$CH$_3$ | CH(CH$_3$)$_2$ | CF$_3$ | CH$_3$ |
| 4.19 | CH$_2$CH$_3$ | CH$_2$CH(CH$_3$)$_2$ | CF$_3$ | CH$_3$ |
| 4.20 | CH$_2$CH$_3$ | CH$_2$C(CH$_3$)$_3$ | CF$_3$ | CH$_3$ |
| 4.21 | CH$_2$CH$_3$ | CH$_3$ | CH$_3$ | CH$_3$ |
| 4.22 | CH$_2$CH$_3$ | CH$_2$CH$_3$ | CH$_3$ | CH$_3$ |
| 4.23 | CH$_2$CH$_3$ | CH(CH$_3$)$_2$ | CH$_3$ | CH$_3$ |
| 4.24 | CH$_2$CH$_3$ | CH$_2$CH(CH$_3$)$_2$ | CH$_3$ | CH$_3$ |
| 4.25 | CH$_2$CH$_3$ | CH$_2$C(CH$_3$)$_3$ | CH$_3$ | CH$_3$ |
| 4.26 | CH$_2$CH$_3$ | CH$_3$ | CH$_2$CH$_3$ | CH$_3$ |
| 4.27 | CH$_2$CH$_3$ | CH$_2$CH$_3$ | CH$_2$CH$_3$ | CH$_3$ |
| 4.28 | CH$_2$CH$_3$ | CH(CH$_3$)$_2$ | CH$_2$CH$_3$ | CH$_3$ |
| 4.29 | CH$_2$CH$_3$ | CH$_2$CH(CH$_3$)$_2$ | CH$_2$CH$_3$ | CH$_3$ |
| 4.30 | CH$_2$CH$_3$ | CH$_2$C(CH$_3$)$_3$ | CH$_2$CH$_3$ | CH$_3$ |
| 4.31 | CH$_2$CH$_2$CH$_3$ | CH$_3$ | CF$_3$ | CH$_3$ |
| 4.32 | CH$_2$CH$_2$CH$_3$ | CH$_2$CH$_3$ | CF$_3$ | CH$_3$ |
| 4.33 | CH$_2$CH$_2$CH$_3$ | CH$_3$ | CH$_3$ | CH$_3$ |
| 4.34 | CH$_2$CH$_2$CH$_3$ | CH$_2$CH$_3$ | CH$_3$ | CH$_3$ |
| 4.35 | CH$_2$CH$_2$CH$_3$ | CH$_3$ | CH$_2$CH$_3$ | CH$_3$ |
| 4.36 | CH$_2$CH$_2$CH$_3$ | CH$_2$CH$_3$ | CH$_2$CH$_3$ | CH$_3$ |
| 4.37 | CH=CH$_2$ | CH$_3$ | CF$_3$ | CH$_3$ |
| 4.38 | CH=CH$_2$ | CH$_2$CH$_3$ | CF$_3$ | CH$_3$ |
| 4.39 | CH=CH$_2$ | CH(CH$_3$)$_2$ | CF$_3$ | CH$_3$ |
| 4.40 | CH=CH$_2$ | CH$_2$CH(CH$_3$)$_2$ | CF$_3$ | CH$_3$ |
| 4.41 | CH=CH$_2$ | CH$_2$C(CH$_3$)$_3$ | CF$_3$ | CH$_3$ |
| 4.42 | CH=CH$_2$ | CH$_3$ | CH$_3$ | CH$_3$ |
| 4.43 | CH=CH$_2$ | CH$_2$CH$_3$ | CH$_3$ | CH$_3$ |
| 4.44 | CH=CH$_2$ | CH(CH$_3$)$_2$ | CH$_3$ | CH$_3$ |
| 4.45 | CH=CH$_2$ | CH$_2$CH(CH$_3$)$_2$ | CH$_3$ | CH$_3$ |
| 4.46 | CH=CH$_2$ | CH$_2$C(CH$_3$)$_3$ | CH$_3$ | CH$_3$ |
| 4.47 | CH=CH$_2$ | CH$_3$ | CH$_2$CH$_3$ | CH$_3$ |
| 4.48 | CH=CH$_2$ | CH$_2$CH$_3$ | CH$_2$CH$_3$ | CH$_3$ |
| 4.49 | CH=CH$_2$ | CH(CH$_3$)$_2$ | CH$_2$CH$_3$ | CH$_3$ |
| 4.50 | CH=CH$_2$ | CH$_2$CH(CH$_3$)$_2$ | CH$_2$CH$_3$ | CH$_3$ |
| 4.51 | CH=CH$_2$ | CH$_2$C(CH$_3$)$_3$ | CH$_2$CH$_3$ | CH$_3$ |
| 4.52 | C≡CH | CH$_3$ | CF$_3$ | CH$_3$ |
| 4.53 | C≡CH | CH$_2$CH$_3$ | CF$_3$ | CH$_3$ |
| 4.54 | C≡CH | CH(CH$_3$)$_2$ | CF$_3$ | CH$_3$ |
| 4.55 | C≡CH | CH$_2$CH(CH$_3$)$_2$ | CF$_3$ | CH$_3$ |
| 4.56 | C≡CH | CH$_2$C(CH$_3$)$_3$ | CF$_3$ | CH$_3$ |
| 4.57 | C≡CH | CH$_3$ | CH$_3$ | CH$_3$ |
| 4.58 | C≡CH | CH$_2$CH$_3$ | CH$_3$ | CH$_3$ |
| 4.59 | C≡CH | CH(CH$_3$)$_2$ | CH$_3$ | CH$_3$ |
| 4.60 | C≡CH | CH$_2$CH(CH$_3$)$_2$ | CH$_3$ | CH$_3$ |

TABLE 4-continued

Compounds of formula ID (ID)

| Compound Number | R$_1$ | R$_2$ | R$_{41}$ | R$_{42}$ |
|---|---|---|---|---|
| 4.61 | C≡CH | CH$_2$C(CH$_3$)$_3$ | CH$_3$ | CH$_3$ |
| 4.62 | C≡CH | CH$_3$ | CH$_2$CH$_3$ | CH$_3$ |
| 4.63 | C≡CH | CH$_2$CH$_3$ | CH$_2$CH$_3$ | CH$_3$ |
| 4.64 | C≡CH | CH(CH$_3$)$_2$ | CH$_2$CH$_3$ | CH$_3$ |
| 4.65 | C≡CH | CH$_2$CH(CH$_3$)$_2$ | CH$_2$CH$_3$ | CH$_3$ |
| 4.66 | C≡CH | CH$_2$C(CH$_3$)$_3$ | CH$_2$CH$_3$ | CH$_3$ |
| 4.67 | C≡CCH$_3$ | CH$_3$ | CF$_3$ | CH$_3$ |
| 4.68 | C≡CCH$_3$ | CH$_2$CH$_3$ | CF$_3$ | CH$_3$ |
| 4.69 | C≡CCH$_3$ | CH(CH$_3$)$_2$ | CF$_3$ | CH$_3$ |
| 4.70 | C≡CCH$_3$ | CH$_2$CH(CH$_3$)$_2$ | CF$_3$ | CH$_3$ |
| 4.71 | C≡CCH$_3$ | CH$_2$C(CH$_3$)$_3$ | CF$_3$ | CH$_3$ |
| 4.72 | C≡CCH$_3$ | CH$_3$ | CH$_3$ | CH$_3$ |
| 4.73 | C≡CCH$_3$ | CH$_2$CH$_3$ | CH$_3$ | CH$_3$ |
| 4.74 | C≡CCH$_3$ | CH(CH$_3$)$_2$ | CH$_3$ | CH$_3$ |
| 4.75 | C≡CCH$_3$ | CH$_2$CH(CH$_3$)$_2$ | CH$_3$ | CH$_3$ |
| 4.76 | C≡CCH$_3$ | CH$_2$C(CH$_3$)$_3$ | CH$_3$ | CH$_3$ |
| 4.77 | C≡CCH$_3$ | CH$_3$ | CH$_2$CH$_3$ | CH$_3$ |
| 4.78 | C≡CCH$_3$ | CH$_2$CH$_3$ | CH$_2$CH$_3$ | CH$_3$ |
| 4.79 | C≡CCH$_3$ | CH(CH$_3$)$_2$ | CH$_2$CH$_3$ | CH$_3$ |
| 4.80 | C≡CCH$_3$ | CH$_2$CH(CH$_3$)$_2$ | CH$_2$CH$_3$ | CH$_3$ |
| 4.81 | C≡CCH$_3$ | CH$_2$C(CH$_3$)$_3$ | CH$_2$CH$_3$ | CH$_3$ |

TABLE 5

Compounds of formula IE (IE)

| Compound Number | R$_1$ | R$_2$ | R$_{51}$ |
|---|---|---|---|
| 5.1 | CH$_3$ | CH$_3$ | Cl |
| 5.2 | CH$_3$ | CH$_2$CH$_3$ | Cl |
| 5.3 | CH$_3$ | CH(CH$_3$)$_2$ | Cl |
| 5.4 | CH$_3$ | CH$_2$CH(CH$_3$)$_2$ | Cl |
| 5.5 | CH$_3$ | CH$_2$C(CH$_3$)$_3$ | Cl |
| 5.6 | CH$_3$ | CH$_3$ | Br |
| 5.7 | CH$_3$ | CH$_2$CH$_3$ | Br |
| 5.8 | CH$_3$ | CH(CH$_3$)$_2$ | Br |
| 5.9 | CH$_3$ | CH$_2$CH(CH$_3$)$_2$ | Br |
| 5.10 | CH$_3$ | CH$_2$C(CH$_3$)$_3$ | Br |
| 5.11 | CH$_3$ | CH$_3$ | CF$_3$ |
| 5.12 | CH$_3$ | CH$_2$CH$_3$ | CF$_3$ |
| 5.13 | CH$_3$ | CH(CH$_3$)$_2$ | CF$_3$ |
| 5.14 | CH$_3$ | CH$_2$CH(CH$_3$)$_2$ | CF$_3$ |
| 5.15 | CH$_3$ | CH$_2$C(CH$_3$)$_3$ | CF$_3$ |
| 5.16 | CH$_2$CH$_3$ | CH$_3$ | Cl |
| 5.17 | CH$_2$CH$_3$ | CH$_2$CH$_3$ | Cl |
| 5.18 | CH$_2$CH$_3$ | CH(CH$_3$)$_2$ | Cl |
| 5.19 | CH$_2$CH$_3$ | CH$_2$CH(CH$_3$)$_2$ | Cl |
| 5.20 | CH$_2$CH$_3$ | CH$_2$C(CH$_3$)$_3$ | Cl |
| 5.21 | CH$_2$CH$_3$ | CH$_3$ | Br |
| 5.22 | CH$_2$CH$_3$ | CH$_2$CH$_3$ | Br |
| 5.23 | CH$_2$CH$_3$ | CH(CH$_3$)$_2$ | Br |
| 5.24 | CH$_2$CH$_3$ | CH$_2$CH(CH$_3$)$_2$ | Br |
| 5.25 | CH$_2$CH$_3$ | CH$_2$C(CH$_3$)$_3$ | Br |
| 5.26 | CH$_2$CH$_3$ | CH$_3$ | CF$_3$ |
| 5.27 | CH$_2$CH$_3$ | CH$_2$CH$_3$ | CF$_3$ |
| 5.28 | CH$_2$CH$_3$ | CH(CH$_3$)$_2$ | CF$_3$ |
| 5.29 | CH$_2$CH$_3$ | CH$_2$CH(CH$_3$)$_2$ | CF$_3$ |
| 5.30 | CH$_2$CH$_3$ | CH$_2$C(CH$_3$)$_3$ | CF$_3$ |
| 5.31 | CH$_2$CH$_2$CH$_3$ | CH$_3$ | Cl |
| 5.32 | CH$_2$CH$_2$CH$_3$ | CH$_2$CH$_3$ | Cl |
| 5.33 | CH$_2$CH$_2$CH$_3$ | CH$_3$ | Br |
| 5.34 | CH$_2$CH$_2$CH$_3$ | CH$_2$CH$_3$ | Br |
| 5.35 | CH$_2$CH$_2$CH$_3$ | CH$_3$ | CF$_3$ |
| 5.36 | CH$_2$CH$_2$CH$_3$ | CH$_2$CH$_3$ | CF$_3$ |
| 5.37 | CH=CH$_2$ | CH$_3$ | Cl |
| 5.38 | CH=CH$_2$ | CH$_2$CH$_3$ | Cl |
| 5.39 | CH=CH$_2$ | CH(CH$_3$)$_2$ | Cl |
| 5.40 | CH=CH$_2$ | CH$_2$CH(CH$_3$)$_2$ | Cl |
| 5.41 | CH=CH$_2$ | CH$_2$C(CH$_3$)$_3$ | Cl |
| 5.42 | CH=CH$_2$ | CH$_3$ | Br |
| 5.43 | CH=CH$_2$ | CH$_2$CH$_3$ | Br |
| 5.44 | CH=CH$_2$ | CH(CH$_3$)$_2$ | Br |
| 5.45 | CH=CH$_2$ | CH$_2$CH(CH$_3$)$_2$ | Br |
| 5.46 | CH=CH$_2$ | CH$_2$C(CH$_3$)$_3$ | Br |
| 5.47 | CH=CH$_2$ | CH$_3$ | CF$_3$ |
| 5.48 | CH=CH$_2$ | CH$_2$CH$_3$ | CF$_3$ |
| 5.49 | CH=CH$_2$ | CH(CH$_3$)$_2$ | CF$_3$ |
| 5.50 | CH=CH$_2$ | CH$_2$CH(CH$_3$)$_2$ | CF$_3$ |
| 5.51 | CH=CH$_2$ | CH$_2$C(CH$_3$)$_3$ | CF$_3$ |
| 5.52 | C≡CH | CH$_3$ | Cl |
| 5.53 | C≡CH | CH$_2$CH$_3$ | Cl |
| 5.54 | C≡CH | CH(CH$_3$)$_2$ | Cl |
| 5.55 | C≡CH | CH$_2$CH(CH$_3$)$_2$ | Cl |
| 5.56 | C≡CH | CH$_2$C(CH$_3$)$_3$ | Cl |
| 5.57 | C≡CH | CH$_3$ | Br |
| 5.58 | C≡CH | CH$_2$CH$_3$ | Br |
| 5.59 | C≡CH | CH(CH$_3$)$_2$ | Br |
| 5.60 | C≡CH | CH$_2$CH(CH$_3$)$_2$ | Br |
| 5.61 | C≡CH | CH$_2$C(CH$_3$)$_3$ | Br |
| 5.62 | C≡CH | CH$_3$ | CF$_3$ |
| 5.63 | C≡CH | CH$_2$CH$_3$ | CF$_3$ |
| 5.64 | C≡CH | CH(CH$_3$)$_2$ | CF$_3$ |
| 5.65 | C≡CH | CH$_2$CH(CH$_3$)$_2$ | CF$_3$ |
| 5.66 | C≡CH | CH$_2$C(CH$_3$)$_3$ | CF$_3$ |
| 5.67 | C≡CCH$_3$ | CH$_3$ | Cl |
| 5.68 | C≡CCH$_3$ | CH$_2$CH$_3$ | Cl |
| 5.69 | C≡CCH$_3$ | CH(CH$_3$)$_2$ | Cl |
| 5.70 | C≡CCH$_3$ | CH$_2$CH(CH$_3$)$_2$ | Cl |
| 5.71 | C≡CCH$_3$ | CH$_2$C(CH$_3$)$_3$ | Cl |
| 5.72 | C≡CCH$_3$ | CH$_3$ | Br |
| 5.73 | C≡CCH$_3$ | CH$_2$CH$_3$ | Br |
| 5.74 | C≡CCH$_3$ | CH(CH$_3$)$_2$ | Br |
| 5.75 | C≡CCH$_3$ | CH$_2$CH(CH$_3$)$_2$ | Br |
| 5.76 | C≡CCH$_3$ | CH$_2$C(CH$_3$)$_3$ | Br |
| 5.77 | C≡CCH$_3$ | CH$_3$ | CF$_3$ |
| 5.78 | C≡CCH$_3$ | CH$_2$CH$_3$ | CF$_3$ |
| 5.79 | C≡CCH$_3$ | CH(CH$_3$)$_2$ | CF$_3$ |
| 5.80 | C≡CCH$_3$ | CH$_2$CH(CH$_3$)$_2$ | CF$_3$ |
| 5.81 | C≡CCH$_3$ | CH$_2$C(CH$_3$)$_3$ | CF$_3$ |

TABLE 6

Compounds of formula IF (IF)

| Compound Number | $R_1$ | $R_2$ | $R_{61}$ |
|---|---|---|---|
| 6.1 | $CH_3$ | $CH_3$ | $CF_3$ |
| 6.2 | $CH_3$ | $CH_2CH_3$ | $CF_3$ |
| 6.3 | $CH_3$ | $CH(CH_3)_2$ | $CF_3$ |
| 6.4 | $CH_3$ | $CH_2CH(CH_3)_2$ | $CF_3$ |
| 6.5 | $CH_3$ | $CH_2C(CH_3)_3$ | $CF_3$ |
| 6.6 | $CH_3$ | $CH_3$ | $CH_3$ |
| 6.7 | $CH_3$ | $CH_2CH_3$ | $CH_3$ |
| 6.8 | $CH_3$ | $CH(CH_3)_2$ | $CH_3$ |
| 6.9 | $CH_3$ | $CH_2CH(CH_3)_2$ | $CH_3$ |
| 6.10 | $CH_3$ | $CH_2C(CH_3)_3$ | $CH_3$ |
| 6.11 | $CH_2CH_3$ | $CH_3$ | $CF_3$ |
| 6.12 | $CH_2CH_3$ | $CH_2CH_3$ | $CF_3$ |
| 6.13 | $CH_2CH_3$ | $CH(CH_3)_2$ | $CF_3$ |
| 6.14 | $CH_2CH_3$ | $CH_2CH(CH_3)_2$ | $CF_3$ |
| 6.15 | $CH_2CH_3$ | $CH_2C(CH_3)_3$ | $CF_3$ |
| 6.16 | $CH_2CH_3$ | $CH_3$ | $CH_3$ |
| 6.17 | $CH_2CH_3$ | $CH_2CH_3$ | $CH_3$ |
| 6.18 | $CH_2CH_3$ | $CH(CH_3)_2$ | $CH_3$ |
| 6.19 | $CH_2CH_3$ | $CH_2CH(CH_3)_2$ | $CH_3$ |
| 6.20 | $CH_2CH_3$ | $CH_2C(CH_3)_3$ | $CH_3$ |
| 6.21 | $CH_2CH_2CH_3$ | $CH_3$ | $CF_3$ |
| 6.22 | $CH_2CH_2CH_3$ | $CH_2CH_3$ | $CF_3$ |
| 6.23 | $CH_2CH_2CH_3$ | $CH_3$ | $CH_3$ |
| 6.24 | $CH_2CH_2CH_3$ | $CH_2CH_3$ | $CH_3$ |
| 6.25 | $CH=CH_2$ | $CH_3$ | $CF_3$ |
| 6.26 | $CH=CH_2$ | $CH_2CH_3$ | $CF_3$ |
| 6.27 | $CH=CH_2$ | $CH(CH_3)_2$ | $CF_3$ |
| 6.28 | $CH=CH_2$ | $CH_2CH(CH_3)_2$ | $CF_3$ |
| 6.29 | $CH=CH_2$ | $CH_2C(CH_3)_3$ | $CF_3$ |
| 6.30 | $CH=CH_2$ | $CH_3$ | $CH_3$ |
| 6.31 | $CH=CH_2$ | $CH_2CH_3$ | $CH_3$ |
| 6.32 | $CH=CH_2$ | $CH(CH_3)_2$ | $CH_3$ |
| 6.33 | $CH=CH_2$ | $CH_2CH(CH_3)_2$ | $CH_3$ |
| 6.34 | $CH=CH_2$ | $CH_2C(CH_3)_3$ | $CH_3$ |
| 6.35 | $C\equiv CH$ | $CH_3$ | $CF_3$ |
| 6.36 | $C\equiv CH$ | $CH_2CH_3$ | $CF_3$ |
| 6.37 | $C\equiv CH$ | $CH(CH_3)_2$ | $CF_3$ |
| 6.38 | $C\equiv CH$ | $CH_2CH(CH_3)_2$ | $CF_3$ |
| 6.39 | $C\equiv CH$ | $CH_2C(CH_3)_3$ | $CF_3$ |
| 6.40 | $C\equiv CH$ | $CH_3$ | $CH_3$ |
| 6.41 | $C\equiv CH$ | $CH_2CH_3$ | $CH_3$ |
| 6.42 | $C\equiv CH$ | $CH(CH_3)_2$ | $CH_3$ |
| 6.43 | $C\equiv CH$ | $CH_2CH(CH_3)_2$ | $CH_3$ |
| 6.44 | $C\equiv CH$ | $CH_2C(CH_3)_3$ | $CH_3$ |
| 6.45 | $C\equiv CCH_3$ | $CH_3$ | $CF_3$ |
| 6.46 | $C\equiv CCH_3$ | $CH_2CH_3$ | $CF_3$ |
| 6.47 | $C\equiv CCH_3$ | $CH(CH_3)_2$ | $CF_3$ |
| 6.48 | $C\equiv CCH_3$ | $CH_2CH(CH_3)_2$ | $CF_3$ |
| 6.49 | $C\equiv CCH_3$ | $CH_2C(CH_3)_3$ | $CF_3$ |
| 6.50 | $C\equiv CCH_3$ | $CH_3$ | $CH_3$ |
| 6.51 | $C\equiv CCH_3$ | $CH_2CH_3$ | $CH_3$ |
| 6.52 | $C\equiv CCH_3$ | $CH(CH_3)_2$ | $CH_3$ |
| 6.53 | $C\equiv CCH_3$ | $CH_2CH(CH_3)_2$ | $CH_3$ |
| 6.54 | $C\equiv CCH_3$ | $CH_2C(CH_3)_3$ | $CH_3$ |

TABLE Z1

Intermediates of formula II (II)

| Compound Number | $R_1$ | $R_2$ |
|---|---|---|
| Z1.1 | $CH_3$ | $CH_3$ |
| Z1.2 | $CH_3$ | $CH_2CH_3$ |
| Z1.3 | $CH_3$ | $CH(CH_3)_2$ |
| Z1.4 | $CH_3$ | $CH_2CH(CH_3)_2$ |
| Z1.5 | $CH_3$ | $CH_2C(CH_3)_3$ |
| Z1.6 | $CH_2CH_3$ | $CH_3$ |
| Z1.7 | $CH_2CH_3$ | $CH_2CH_3$ |
| Z1.8 | $CH_2CH_3$ | $CH(CH_3)_2$ |
| Z1.9 | $CH_2CH_3$ | $CH_2CH(CH_3)_2$ |
| Z1.10 | $CH_2CH_3$ | $CH_2C(CH_3)_3$ |
| Z1.11 | $CH_2CH_2CH_3$ | $CH_3$ |
| Z1.12 | $CH_2CH_2CH_3$ | $CH_2CH_3$ |
| Z1.13 | $CH=CH_2$ | $CH_3$ |
| Z1.14 | $CH=CH_2$ | $CH_2CH_3$ |
| Z1.15 | $CH=CH_2$ | $CH(CH_3)_2$ |
| Z1.16 | $CH=CH_2$ | $CH_2CH(CH_3)_2$ |
| Z1.17 | $CH=CH_2$ | $CH_2C(CH_3)_3$ |
| Z1.18 | $CH=CHCH_3$ | $CH_3$ |
| Z1.19 | $CH=CHCH_3$ | $CH_2CH_3$ |
| Z1.20 | $CH=CHCH_3$ | $CH(CH_3)_2$ |
| Z1.21 | $CH=CHCH_3$ | $CH_2CH(CH_3)_2$ |
| Z1.22 | $CH=CHCH_3$ | $CH_2C(CH_3)_3$ |
| Z1.23 | $C\equiv CH$ | $CH_3$ |
| Z1.24 | $C\equiv CH$ | $CH_2CH_3$ |
| Z1.25 | $C\equiv CH$ | $CH(CH_3)_2$ |
| Z1.26 | $C\equiv CH$ | $CH_2CH(CH_3)_2$ |
| Z1.27 | $C\equiv CH$ | $CH_2C(CH_3)_3$ |
| Z1.28 | $C\equiv CCH_3$ | $CH_3$ |
| Z1.29 | $C\equiv CCH_3$ | $CH_2CH_3$ |
| Z1.30 | $C\equiv CCH_3$ | $CH(CH_3)_2$ |
| Z1.31 | $C\equiv CCH_3$ | $CH_2CH(CH_3)_2$ |
| Z1.32 | $C\equiv CCH_3$ | $CH_2C(CH_3)_3$ |

Physical Data (Melting Points in ° C.):

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

Table 7 shows selected melting point and selected NMR data, all with $CDCl_3$ as the solvent (unless otherwise stated; if a mixture of solvents is present, this is indicated as, for example, ($CDCl_3/d_6$-DMSO)), (no attempt is made to list all characterising data in all cases) for compounds of Tables 1 to 6 and Z1.

TABLE 8

| Compound Number | $^1$H-NMR data: (ppm/multiplicity/number of Hs). | m.p./ (° C.) |
|---|---|---|
| 1.1 | | resin |
| 1.2 | | 147-150 |
| 1.6 | | wax |
| 1.7 | | 123-126 |
| 1.26 | | 187-187 |
| 1.27 | | 158-159 |
| 1.31 | | 162-164 |
| 1.32 | | 115-116 |
| 1.51 | | 176-177 |
| 1.53 | | 149-150 |
| 1.61 | | 118-119 |
| 1.62 | | 95-96 |
| 1.66 | | 114-115 |
| 1.67 | | 93-96 |
| 1.111 | | 85-87 |
| 1.116 | | 101-103 |
| 2.1 | | 180-185 |
| 2.2 | | 185-188 |
| 2.26 | | 134-134 |
| 2.27 | | 160-163 |
| 2.51 | | 167-168 |
| 2.62 | | resin |
| 2.66 | | wax |
| 2.111 | | 59-61 |
| 3.1 | | resin |
| 4.1 | | 146-147 |
| 4.2 | | 90-92 |
| 4.16 | | 179-181 |
| 4.17 | | 128-130 |
| 4.31 | | 166-168 |
| 4.37 | | 139-140 |
| 4.67 | | 90-91 |
| 5.1 | | 116-117 |
| 5.16 | | 137-138 |
| 5.17 | | 127-128 |
| 5.31 | | 163-164 |
| 5.37 | | 126-127 |
| 5.67 | | 84-86 |
| 6.6 | | resin |
| Z1.1 | 1.41(s, 9H), 2.39 (s, 3H), 3.57 (s(broad), 2H), 6.61 (d, 1H), 6.85(d, 1H), 6.98 (tr, 1H) | oil |
| Z1.2 | 0.69 (tr, 3H), 1.37 (s, 6H), 1.81 (q, 2H), 2.26 (s, 3H), 3.55 (s(broad), 2H), 6.61 (d, 1H), 6.79 (d, 1H), 6.96 (tr, 1H) | oil |
| Z1.6 | 1.20 (tr, 3H), 1.41 (s, 9H), 2.84 (q, 2H), 3.64 (s(broad), 2H), 6.59 (d, 1H), 6.85 (dd, 1H), 6.97 (tr, 1H) | oil |
| Z1.7 | 0.70 (tr, 3H), 1.18 (tr, 3H), 1.37 (s, 6H), 1.78 (q, 2H), 3.62 (s(broad), 2H), 6.60 (dd, 1H), 6.78 (dd, 1H), 6.95 (tr, 1H) | oil |
| Z1.11 | 1.06 (tr, 3H), 1.40 (s, 9H), 1.60 (m, 2H), 2.71 (m, 2H), 3.63 (s(broad), 2H), 6.60 (dd, 1H), 6.85 (dd, 1H), 6.96 (tr, 1H) | oil |
| Z1.13 | 1.37 (s, 9H), 3.85 (s(broad), 2H), 5.36 (dd, 1H), 5.64 (dd, 1H), 6.62 (dd, 1H), 6.8-7.05 (m, 3H) | oil |
| Z1.14 | 0.65 (tr, 3H), 1.32 (s, 6H), 1.75 (q, 2H), 3.83 (s(broad), 2H), 5.33 (dd, 1H), 5.90 (dd, 1H), 6.60 (d, 1H), 6.75 (dd, 1H), 6.80 (m, 1H), 7.00 (tr, 1H) | oil |
| Z1.28 | 1.47 (s, 9H), 2.16 (s, 3H), 4.27 (s(broad), 2H), 6.59 (dd, 1H), 6.73 (dd, 1H), 7.00 (tr, 1H) | oil |
| Z1.29 | | oil |

FORMULATION EXAMPLES FOR COMPOUNDS OF FORMULA I

Example F-1.1 to F-1.3

Emulsifiable Concentrates

| Components | F-1.1 | F-1.2 | F-1.3 |
|---|---|---|---|
| compound of Tables 1 to 6 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r.h. plants are kept in a greenhouse for 8 days at 20° C. and 60% r.h. The disease incidence is assessed 10 days after inoculation. Compounds of Tables 1-6 show good activity in this test (<20% infestation).

Example B-2

Action Against *Podosphaera leucotricha*/Apple (Powdery Mildew on Apple)

5 week old apple seedlings cv. Mcintosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed. Compounds of Tables 1-6 show good activity in this test (<20% infestation).

Example B-3

Action Against *Venturia inaegualis*/Apple (Scab on Apple)

4 week old apple seedlings cv. Mcintosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation

Example B-4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r.h. in a greenhouse the disease incidence is assessed. Compounds of Tables 1-6 show good activity in this test (<20% infestation).

Example B-5

Action Against *Botrytis cinerea*/Apple (Botrytis on Apple Fruits)

In an apple fruit cv. Golden Delicious 3 holes are drilled and each filled with 30 µl droplets of the formulated test compound (0.002% active ingredient). Two hours after application 50 µl of a spore suspension of *B. cinerea* ($4 \times 10^5$ conidia/ml) are pipetted on the application sites. After an incubation period of 7 days at 22° C. in a growth chamber the disease incidence is assessed. Compounds of Tables 1-6 show good activity in this test (<20% infestation).

Example B-6

Action Against *Botrytis cinerea*/grape (Botrytis on Grapes)

5 week old grape seedlings cv. Gutedel are treated with the formulated test compound (0.002% active ingredient) in a spray chamber. Two days after application grape plants are inoculated by spraying a spore suspension ($1 \times 10^6$ conidia/ml) on the test plants. After an incubation period of 4 days at 21° C. and 95% r.h. in a greenhouse the disease incidence is assessed. Compounds of Tables 1-6 show good activity in this test (<20% infestation).

Example B-7

Action against *Botrytis cinerea*/Tomato (Botrytis on Tomatoes)

4 week old tomato plants cv. Roter Gnom are treated with the formulated test compound (0.002% active ingredient) in a spray chamber. Two days after application tomato plants are inoculated by spraying a spore suspension ($1 \times 10^5$ conidia/ml) on the test plants. After an incubation period of 4 days at 20° C. and 95% r.h. in a growth chamber the disease incidence is assessed. Compounds of Tables 1-6 show good activity in this test (<20% infestation).

Example B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation. Compounds of Tables 1-6 show good activity in this test (<20% infestation).

Example B-9

Action Against *Septoria tritici*/Wheat (Septoria Leaf Spot on Wheat)

2 week old wheat plants cv. Riband are treated with the formulated test compound (0.2% active ingredient) in a spray chamber. One day after application, wheat plants are inoculated by spraying a spore suspension ($10 \times 10^5$ conidia/ml) on the test plants. After an incubation period of 1 day at 23° C. and 95% r.h., the plants are kept for 16 days at 23° C. and 60% r.h. in a greenhouse. The disease incidence is assessed 18 days after inoculation.

Compounds of Tables 1-6 show good activity in this test (<20% infestation).

Example B-10

Action Against *Uncinula necator*/Grape (Powdery Mildew on Grape)

5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% r.h. under a light regime of 14/10 hours (light/dark) the disease incidence is assessed. Compounds of Tables 1-6 show good activity in this test (<20% infestation).

Example B-11

Action Against *Alternaria solanil* Tomato (Early Blight on Tomatoes)

4 week old tomato plants cv. Roter Gnom are treated with the formulated test compound (0.02% active ingredient) in a spray chamber. Two days after application, the tomato plants are inoculated by spraying a spore suspension ($2 \times 10^5$ conidia/ml) on the test plants. After an incubation period of 3 days at 20° C. and 95% r.h. in a growth chamber the disease incidence is assessed. Compounds of Tables 1-6 show good activity in this test (<20% infestation).

Example B-12

Action Against *Ustilago nuda*/Barley

After application of the active ingredient formulated as a flowable concentrate for seed treatment onto *U. nuda*-infected seeds of winterbarley (0.02% active ingredient) the seeds are sown in trays filled with field soil. The trays are transferred to a growth room and kept there for 2 days at 20° C. and then for 2 weeks at 2° C. After this period the trial is transferred to a greenhouse where a temperature of 15° C. and a 14 hr light period is provided until flowering. The disease incidence is assessed as number of infected heads. Compounds of Tables 1-6 show good activity in this test (<20% infestation).

What is claimed is:

1. A compound of the formula I

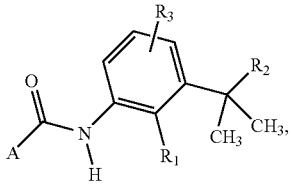

in which
R$_1$ is a C$_1$-C$_4$alkyl, C$_2$-C$_4$alkenyl or C$_2$-C$_4$alkynyl group; or
R$_1$ is a C$_1$-C$_4$alkyl, C$_2$-C$_4$alkenyl or C$_2$-C$_4$alkynyl group which is mono- or polysubstituted by halogen, hydroxy, cyano, C$_1$-C$_4$alkoxycarbonyl, formyl, nitro, C$_1$-C$_4$alkoxy, C$_1$-C$_4$haloalkoxy, C$_1$-C$_4$alkylthio, C$_1$-C$_4$haloalkylthio, HC(OR$_4$)=N— and/or R$_5$R$_6$NN=C(H)—;
R$_4$, R$_5$ and R$_6$ independently of one another are hydrogen or C$_1$-C$_4$alkyl;
R$_2$ is a C$_1$-C$_6$alkyl group; or
R$_2$ is a C$_1$-C$_6$alkyl group which is mono- or polysubstituted by halogen, hydroxy, cyano, C$_1$-C$_4$alkoxycarbonyl, formyl, nitro, C$_1$-C$_4$alkoxy, C$_1$-C$_4$haloalkoxy, C$_1$-C$_4$alkylthio, C$_1$-C$_4$haloalkylthio, HC(OR$_7$)=N— or R$_8$R$_9$NN=C(H)—;
R$_7$, R$_8$ and R$_9$ independently of one another are hydrogen or C$_1$-C$_4$alkyl;
R$_3$ is hydrogen or halogen; and
A is A$_1$

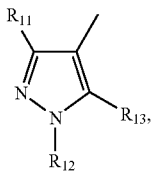

in which
R$_{11}$, R$_{12}$ and R$_{13}$ independently of one another are selected from hydrogen, halo, cyano, nitro, C$_1$-C$_4$alkyl, C$_1$-C$_4$haloalkyl, C$_1$-C$_4$alkoxy- C$_1$-C$_4$alkyl and C$_1$-C$_4$haloalkoxy-C$_1$-C$_4$alkyl, provided that at least one of R$_{11}$, R$_{12}$ and R$_{13}$ is not hydrogen;
or a tautomer or an enantiomer of these compounds.

2. A method of controlling or preventing infestation of useful plants by phytopathogenic microorganisms, wherein a compound of formula I according to claim 1 or a composition comprising the compound of formula I as an active ingredient is applied to the plants, to parts thereof or the locus thereof.

3. A composition for controlling and protecting a plant against phytopathogenic microorganisms, said composition comprising a compound of formula I according to claim 1 and an inert carrier.

4. The compound of claim 1, wherein R$_{11}$, R$_{12}$ and R$_{13}$ independently of one another are selected from hydrogen, C$_1$-C$_4$alkyl, C$_1$-C$_4$haloalkyl.

5. The compound of claim 4, wherein R$_1$ is a C$_2$-C$_4$alkenyl and R$_2$ is a C$_1$-C$_6$alkyl group.

6. The compound of claim 5, wherein said compound comprises 1-methyl-3-trifluoromethyl-1-H-pyrazole-4-carboxylic acid (3-tert-butyl-2-vinylphenyl)amide.

7. The method of claim 2, wherein R$_{11}$, R$_{12}$ and R$_{13}$ independently of one another are selected from hydrogen, C$_1$-C$_4$alkyl, C$_1$-C$_4$haloalkyl.

8. The method of claim 7, wherein R$_1$ is a C$_2$-C$_4$alkenyl and R$_2$ is a C$_1$-C$_6$alkyl group.

9. The method of claim 8, wherein said compound comprises 1-methyl-3-trifluoromethy-1H-pyrazole-4-carboxylic acid (3-tert-butyl-2-vinylphenyl)amide.

10. The composition of claim 3, wherein R$_{11}$, R$_{12}$ and R$_{13}$ independently of one another are selected from hydrogen, C$_1$-C$_4$alkyl, C$_1$-C$_4$haloalkyl.

11. The composition of claim 10, wherein R$_1$ is a C$_2$-C$_4$alkenyl and R$_2$ is a C$_1$-C$_6$alkyl group.

12. The composition of claim 11, wherein said compound comprises 1-methyl-3-trifluoromethy-1H-pyrazole-4-carboxylic acid (3-tert-butyl-2-vinylphenyl)amide.

13. A compound of the formula I

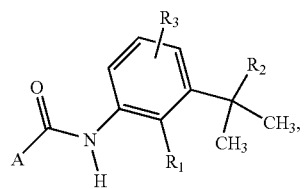

in which
R$_1$ is a C$_1$-C$_4$alkyl, C$_2$-C$_4$alkenyl or C$_2$-C$_4$alkynyl group; or
R$_1$ is a C$_1$-C$_4$alkyl, C$_2$-C$_4$alkenyl or C$_2$-C$_4$alkynyl group which is mono- or polysubstituted by halogen, hydroxy, cyano, C$_1$-C$_4$alkoxycarbonyl, formyl, nitro, C$_1$-C$_4$alkoxy, C$_1$-C$_4$haloalkoxy, C$_1$-C$_4$alkylthio, C$_1$-C$_4$haloalkylthio, HC(OR$_4$)=N— or R$_5$R$_6$NN=C(H)—;
R$_4$, R$_5$ and R$_6$ independently of one another are hydrogen or C$_1$-C$_4$alkyl;
R$_2$ is a C$_1$-C$_6$alkyl group; or
R$_2$ is a C$_1$-C$_6$alkyl group which is mono- or polysubstituted by halogen, hydroxy, cyano, C$_1$-C$_4$alkoxycarbonyl, formyl, nitro, C$_1$-C$_4$alkoxy, C$_1$-C$_4$haloalkoxy, C$_1$-C$_4$alkylthio, C$_1$-C$_4$haloalkylthio, HC(OR$_7$)=N— or R$_8$R$_9$NN=C(H)—;
R$_7$, R$_8$ and R$_9$ independently of one another are hydrogen or C$_1$-C$_4$alkyl;
R$_3$ is hydrogen or halogen;
A is A$_1$

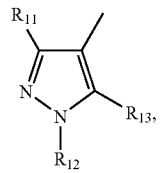

in which
R$_{11}$ and R$_{12}$ independently of one another are selected from hydrogen, halo, cyano, nitro, C$_1$-C$_4$alkyl, C$_1$-C$_4$haloalkyl, C$_1$-C$_4$alkoxy-C$_1$-C$_4$alkyl and $C_1$-$C_4$haloalkoxy-$C_1$-$C_4$alkyl, provided that at least one of $R_{11}$ and $R_{12}$ is not hydrogen; and $R_{13}$ is hydrogen;

or a tautomer or an enantiomer of these compounds.

14. A method of controlling or preventing infestation of useful plants by phytopathogenic microorganisms, wherein a compound of formula I according to claim 13 or a composition comprising the compound of formula I as an active ingredient is applied to the plants, to parts thereof or the locus thereof.

15. A composition for controlling and protecting a plant against phytopathogenic microorganisms, said composition comprising a compound of formula I according to claim 13 and an inert carrier.

16. A compound of the formula I

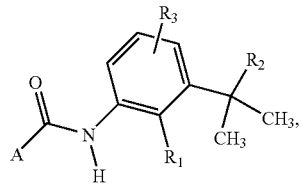

(I)

in which $R_1$ is a $C_1$-$C_4$alkyl, $C_2$-$C_4$alkenyl or $C_2$-$C_4$alkynyl group; or $R_1$ is a $C_1$-$C_4$alkyl, $C_2$-$C_4$alkenyl or $C_2$-$C_4$alkynyl group which is mono- or polysubstituted by halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$_4$)=N— or $R_5R_6$NN=C(H)—;

$R_4$, $R_5$ and $R_6$ independently of one another are hydrogen or $C_1$-$C_4$alkyl;

$R_2$ is a $C_1$-$C_6$alkyl group; or $R_2$ is a $C_1$-$C_6$alkyl group which is mono- or polysubstituted by halogen, hydroxy, cyano, $C_1$-$C_4$alkoxycarbonyl, formyl, nitro, $C_1$-$C_4$alkoxy, $C_1$-$C_4$haloalkoxy, $C_1$-$C_4$alkylthio, $C_1$-$C_4$haloalkylthio, HC(OR$_7$)=N— or $R_8R_9$NN=C(H)—;

$R_7$, $R_8$ and $R_9$ independently of one another are hydrogen or $C_1$-$C_4$alkyl;

$R_3$ is hydrogen or halogen;

A is $A_1$

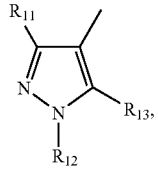

($A_1$)

in which $R_{11}$ is selected from $C_1$-$C_4$alkyl or $C_1$-$C_4$haloalkyl;

$R_{12}$ is selected from $C_1$-$C_4$alkyl; and $R_{13}$ is hydrogen or halogen;

or a tautomers or an enantiomers of these compounds.

17. The compound of claim 16, wherein $R_{13}$ is hydrogen.

18. The compound of claim 16, wherein $R_{13}$ is halogen.

19. A method of controlling or preventing infestation of useful plants by phytopathogenic microorganisms, wherein a compound of formula I according to claim 16 or a composition comprising the compound of formula I as an active ingredient is applied to the plants, to parts thereof or the locus thereof.

20. A composition for controlling and protecting a plant against phytopathogenic microorganisms, said composition comprising a compound of formula I according to claim 16 and an inert carrier.

* * * * *